US012599597B2

(12) United States Patent
Liu et al.

(10) Patent No.: US 12,599,597 B2
(45) Date of Patent: Apr. 14, 2026

(54) SUBSTITUTED N-BENZHYDRYLACETAMIDE INHIBITORS OF JUMANJI DOMAIN HISTONE DEMETHYLASES FOR THE TREATMENT OF CANCER

(71) Applicant: University of Kentucky Research Foundation, Lexington, KY (US)

(72) Inventors: Chunming Liu, Lexington, KY (US); David S. Watt, Lexington, KY (US); Wen Zhang, Lexington, KY (US); Vitaliy M. Sviripa, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 548 days.

(21) Appl. No.: 17/907,943

(22) PCT Filed: Mar. 4, 2021

(86) PCT No.: PCT/US2021/020949

§ 371 (c)(1),
(2) Date: Aug. 29, 2022

(87) PCT Pub. No.: WO2021/178721

PCT Pub. Date: Sep. 10, 2021

(65) Prior Publication Data

US 2023/0108479 A1 Apr. 6, 2023

Related U.S. Application Data

(60) Provisional application No. 62/985,186, filed on Mar. 4, 2020.

(51) Int. Cl.

*A61K 31/4709* (2006.01)
*A61K 31/47* (2006.01)
*A61P 35/00* (2006.01)

(52) U.S. Cl.

CPC .......... *A61K 31/4709* (2013.01); *A61K 31/47* (2013.01); *A61P 35/00* (2018.01)

(58) Field of Classification Search

CPC ...... A61K 31/4709; A61K 31/47; A61P 35/00
See application file for complete search history.

(56) References Cited

U.S. PATENT DOCUMENTS 11,497,740 B2 11/2022 Dalvi et al.
11,701,374 B1 7/2023 Andrews et al.
2008/0312278 A1 12/2008 Schadt et al.
2012/0295890 A1 11/2012 Crawford et al.
2013/0096159 A1* 4/2013 Maloney .................. A61P 9/00 546/175
2019/0151306 A1 5/2019 Szakács et al.

FOREIGN PATENT DOCUMENTS

EP 3388419 A1 * 10/2018 .......... C07D 215/28
WO WO-2008014602 A1 * 2/2008 .......... C07D 215/26
WO WO 2010-014948 A1 2/2010
WO WO-2010068767 A1 * 6/2010 ................ A61P 3/10
WO WO-2011082175 A2 * 7/2011 ............. A61P 35/00
WO WO 2011-146618 A1 11/2011

OTHER PUBLICATIONS

Poloznikov, A. A., et al. "Structure-activity relationship for branched oxyquinoline HIF activators: Effect of modifications to phenylacetamide "tail"." Biochimie 133 (2017): 74-79. (Year: 2017).*
Serrao, Erik, et al. "Fragment-based discovery of 8-hydroxyquinoline inhibitors of the hiv-1 integrase-lens epithelium-derived growth factor/p75 (in-ledgf/p75) interaction." Journal of medicinal chemistry 56.6 (2013): 2311-2322. (Year: 2013).*
Kenyon, Victor, et al. "Discovery of potent and selective inhibitors of human platelet-type 12-lipoxygenase." Journal of medicinal chemistry 54.15 (2011): 5485-5497. (Year: 2011).*
Korean Intellectual Property Office, International Search Report and Written Opinion issued in corresponding Application No. PCT/US2021/020949, mailed Jul. 2, 2021.
Coombs, GS et al, "Modulation of Wnt/p-catenin signaling and proliferation by a ferrous iron chelator with therapeutic efficacy in genetically engineered mouse models of cancer", Oncogene, 2012, vol. 31, pp. 213-225.
Zhang, W. et al., "Epigenetic Regulation of Wnt Signaling by Carboxamide-Substituted Benzhydryl Amines that Function as Histone Demethylase Inhibitors", iScience, Dec. 18, 2020, vol. 23, article No. 101795, pp. 1-12 and Supplemental Information.
United States Patent and Trademark Office, International Search Report and Written Opinion issued for PCT/US2025/026024, mailed Aug. 20, 2025.
Pubchem, SID 482263650, Modify Date: Jun. 28, 2023 [retrieved on Jun. 15, 2025]., Retrieved from the Internet <URL: https://pubchem.ncbi.nlm.nih.gov/substance/482263650>.
Pubchem, SID 105355005, Modify Date: Jun. 28, 2023 [retrieved on Jun. 5, 2025]., Retrieved from the Internet <URL: https://pubchem.ncbi.nlm.nih.gov/substance/105355005>.
Peng, K.; Su, G.; Ji, J.; Yang, X.; Miao, M.; Mo, P.; Li, M.; Xu, J.; Li, W.; Yu, C., Histone demethylase JMJD1A promotes colorectal cancer growth and metastasis by enhancing Wnt/beta-catenin signaling. J Biol Chem 2018, 293 (27), 10606-10619.

(Continued)

*Primary Examiner* — Kamal A Saeed
*Assistant Examiner* — Quincy Mckoy
(74) *Attorney, Agent, or Firm* — Stites & Harbison PLLC; Gary N. Stewart; Mandy Wilson Decker

(57) ABSTRACT

Provided herein are compounds for inhibiting Wnt signaling and methods of treating cancer. The compounds include any compound having a structure according to Formula II. The method includes administering one or more compounds according to Formula I and/or Formula II to a subject in need thereof.

10 Claims, 10 Drawing Sheets

(56) References Cited

OTHER PUBLICATIONS

Liu, J.; Liang, T.; Zhangsun, W., KDM3A is associated with tumor metastasis and modulates colorectal cancer cell migration and invasion. Int J Biol Macromol 2019, 126, 318-325.

Li, J.; Yu, B.; Deng, P.; Cheng, Y.; Yu, Y.; Kevork, K.; Ramadoss, S.; Ding, X.; Li, X.; Wang, C. Y., KDM3 epigenetically controls tumorigenic potentials of human colorectal cancer stem cells through Wnt/beta-catenin signalling. Nat Commun 2017, 8, 15146.

Wang, H. Y.; Long, Q. Y.; Tang, S. B.; Xiao, Q.; Gao, C.; Zhao, Q. Y.; Li, Q. L.; Ye, M.; Zhang, L.; Li, L. Y.; Wu, M., Histone demethylase KDM3A is required for enhancer activation of hippo target genes in colorectal cancer. Nucleic Acids Res 2019, 47 (5), 2349-2364.

Wilson, S.; Fan, L.; Sahgal, N.; Qi, J.; Filipp, F. V., The histone demethylase KDM3A regulates the transcriptional program of the androgen receptor in prostate cancer cells. Oncotarget, 2017, vol. 8, (No. 18), pp. 30328-30343.

Sarac, H.; Morova, T.; Pires, E.; Mcullagh, J.; Kaplan, A.; Cingöz, A; Bagci-Onder, T.; Önder, T.; Kawamura, A.; Lack, N. A., Systematic characterization of chromatin modifying enzymes identifies KDM3B as a critical regulator in castration resistant prostate cancer. Oncogene (2020) 39:2187-2201.

Zhang, W.; Sviripa, V. M.; Xie, Y.; Yu, T.; Haney, M. G.; Blackburn, J. S.; Adeniran, C. A.; Zhan, C. G.; Watt, D. S.; Liu, C., Epigenetic Regulation of Wnt Signaling by Carboxamide-Substituted Benzhydryl Amines that Function as Histone Demethylase Inhibitors. iScience 2020, 23 (12), 101795.

* cited by examiner

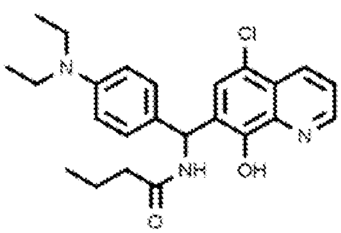

VMS-7-133: N-((5-chloro-8-hydroxyquinolin-7-yl)(4-(diethylamino)phenyl)methyl)butyramide

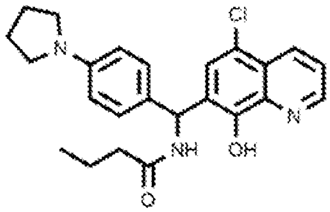

VMS-7-161: N-((5-chloro-8-hydroxyquinolin-7-yl)(4-(pyrrolidin-1-yl)phenyl)methyl)butyramide

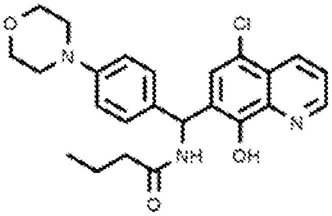

VMS-7-163: N-((5-chloro-8-hydroxyquinolin-7-yl)(4-morpholinophenyl)methyl)butyramide

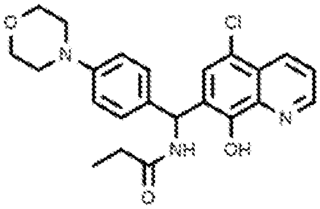

VMS-7-164: N-((5-chloro-8-hydroxyquinolin-7-yl)(4-morpholinophenyl)methyl)propionamide

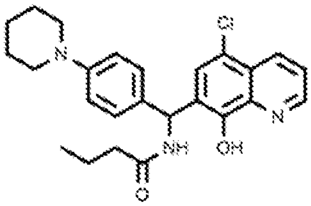

VMS-7-165: N-((5-chloro-8-hydroxyquinolin-7-yl)(4-(piperidin-1-yl)phenyl)methyl)butyramide

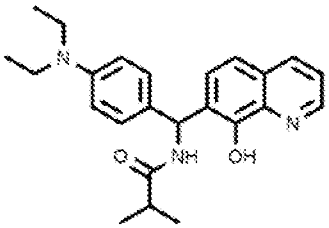

VMS-7-174: N-((4-(diethylamino)phenyl)(8-hydroxyquinolin-7-yl)methyl)isobutyramide

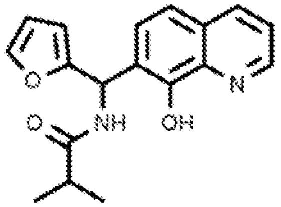

VMS-7-175: N-((4-(diethylamino)phenyl)(8-hydroxyquinolin-7-yl)methyl)isobutyramide

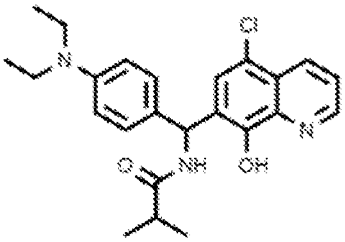

VMS-7-176: N-((5-chloro-8-hydroxyquinolin-7-yl)(4-(diethylamino)phenyl)methyl)-isobutyramide

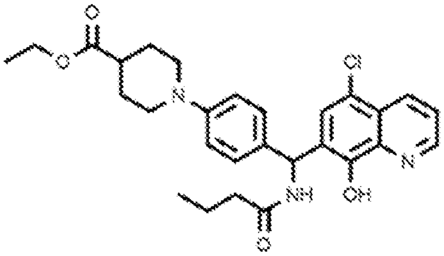

VMS-7-183: Ethyl 1-(4-(butyramido(5-chloro-8-hydroxyquinolin-7-yl)methyl)phenyl)piperidine-4-carboxylate

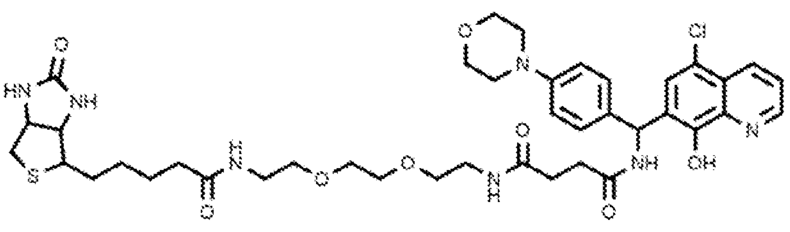

VMS-7-195: N1-((5-chloro-8-hydroxyquinolin-7-yl)(4-morpholinophenyl)methyl)-N4-(2-(2-(2-(5-(2-oxohexahydro-1H-thieno[3,4-d]imidazol-4-yl)pentanamido)ethoxy)ethoxy)ethyl)succinamide

FIG. 3B

CBA-B2

SUBSTITUTED N-BENZHYDRYLACETAMIDE INHIBITORS OF JUMANJI DOMAIN HISTONE DEMETHYLASES FOR THE TREATMENT OF CANCER

RELATED APPLICATIONS

This application is a national stage application of International Patent Application No. PCT/US2021/20949 filed Mar. 4, 2021 which claims the benefit of U.S. Provisional Application Ser. No. 62/985,186 filed Mar. 4, 2020, the entire disclosure of which is incorporated herein by this reference.

GOVERNMENT INTEREST

This invention was made with government support under grant number P30 GM110787 and R01 CA172379 awarded by the National Institutes of Health (NIH). The government has certain rights in the invention.

TECHNICAL FIELD

The present invention relates to compounds that function as epigenetic regulators and thereby inhibit Wnt signaling and methods of use thereof. In particular, the presently-disclosed subject matter relates to substituted N-benzhydrylacetamide compounds and the use thereof to treat cancers in which Wnt signaling is upregulated.

BACKGROUND

Wnt signaling is a key target for multiple human cancers, including but not limited to colon cancer, liver cancer and lung cancer. For example, a majority of colorectal cancer (CRC) cases, which are the second leading cause of cancer-related mortality in the United States, involve mutations in the Wnt signaling pathway. These mutations are found primarily in the Adenomatous Polyposis Coli (APC) gene or the CTNNB1 (beta-catenin) gene, where they stabilize beta-catenin and promote cancer proliferation.

The crucial roles of Wnt signaling in CRC progression make it an important, potential target for the development of new anticancer agents. However, while research in this area is ongoing, prior efforts have focused on targets upstream of beta-catenin. For example, a tankyrase inhibitor, XAV939, stabilizes Axin and induces β-catenin degradation. Porcupine (PORCN) inhibitors, IWP2 and LSK-974, inhibit Wnt processing and secretion. These agents may inhibit Wnt signaling in normal cells; but, unfortunately, are ineffectual for CRC cells containing Wnt pathway mutations. As such, despite decades of research and clinical studies, there remains a need in the art for Wnt signaling inhibitors, and particularly inhibitors that work downstream of beta-catenin and thus inhibit CRC cells with APC and CTNNB1 mutations.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a compound for inhibiting Wnt signaling, the compound comprising a structure according to Formula II:

II

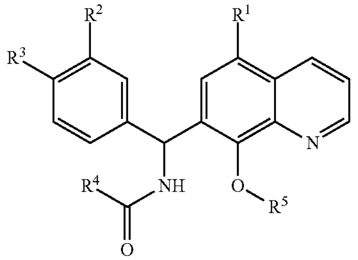

analogs thereof, or combinations thereof; where $R^1$ includes H, Cl, or nitrite; $R^2$ includes H or alkoxy; $R^3$ includes substituted or unsubstituted, branched or unbranched alkyl, alkoxy, amino, halogen, heterocycle, or combinations thereof; $R^4$ includes substituted or unsubstituted, branched or unbranched alkyl; and $R^5$ includes H or methyl carbonyl.

In some embodiments, $R^1$ is Cl. In some embodiments, $R^5$ is H. In some embodiments, $R^2$ is H. In some embodiments, $R^4$ is an unbranched alkyl. In some embodiments, $R^4$ is a branched alkyl. In some embodiments $R^3$ is an unbranched alkyl. In some embodiments, $R^3$ is an unbranched alkyl. In some embodiments, $R^3$ is a branched alkyl. In some embodiments, $R^3$ is an unbranched alkoxy. In some embodiments, $R^3$ is a branched amino. In some embodiments, $R^3$ is a heterocycle. In some embodiments, the heterocycle is selected from the group consisting of pyrrolidinyl, piperidinyl, and morpholino. In some embodiments, $R^3$ is a halogen.

In some embodiments, the compound includes:
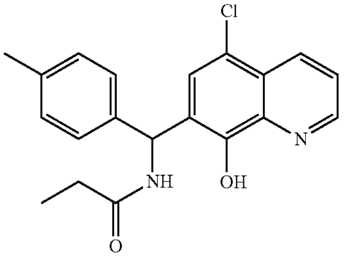,
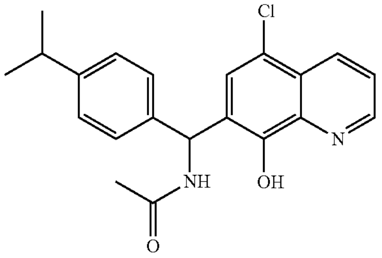,
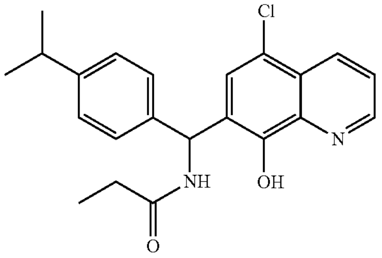,
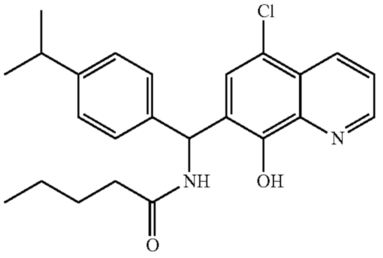,
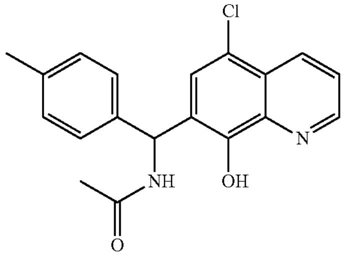,
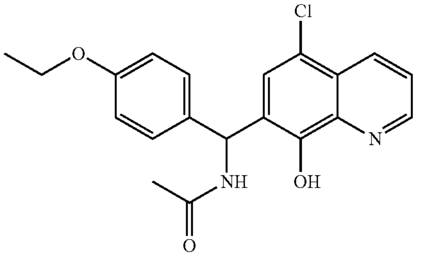,
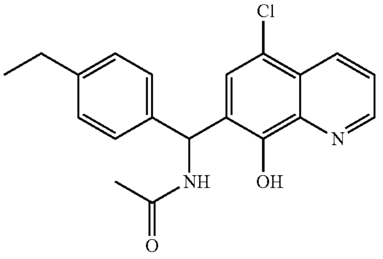,
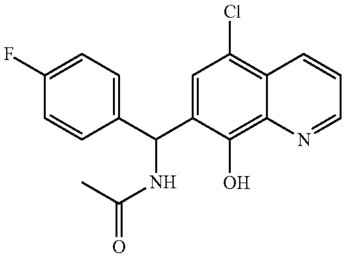,
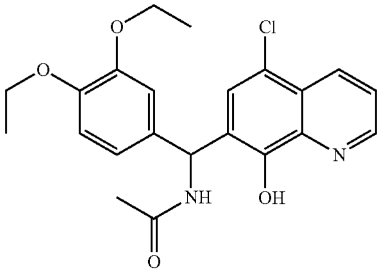,
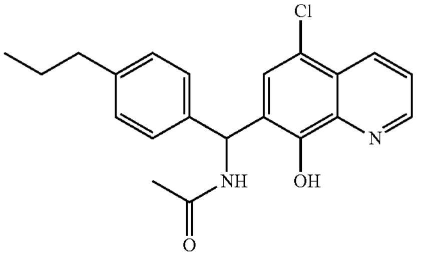,
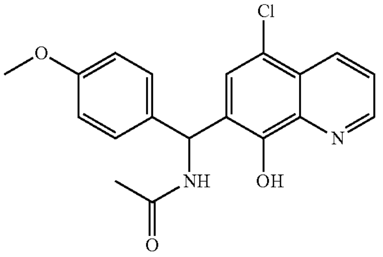,
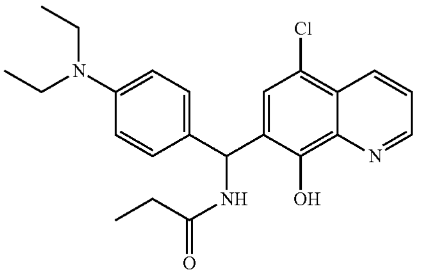,
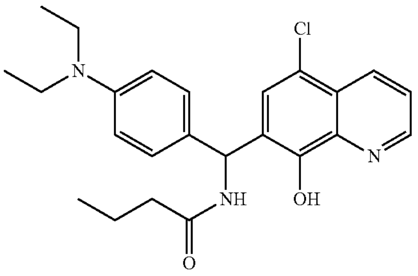, -continued
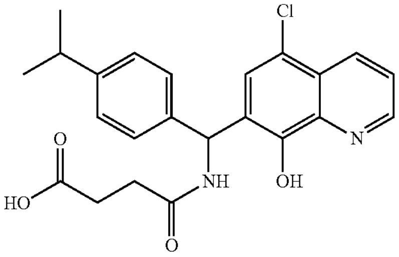,
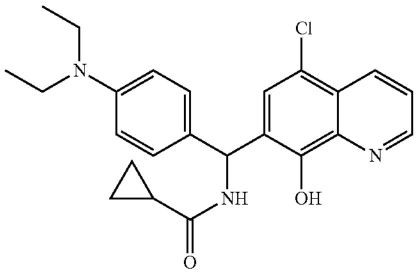,
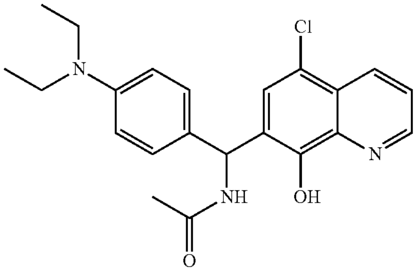,
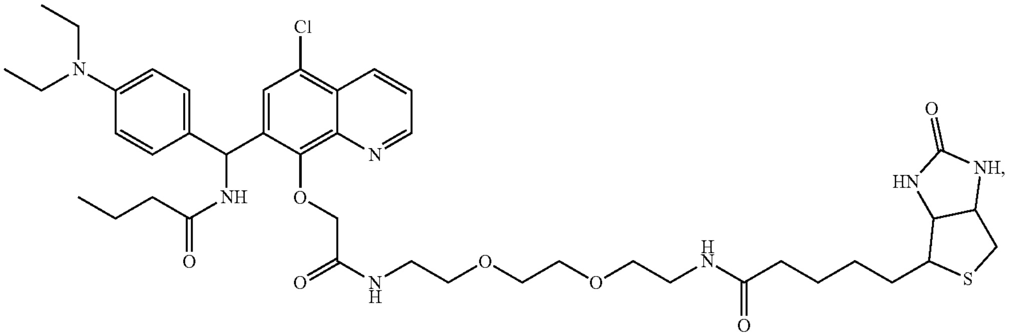
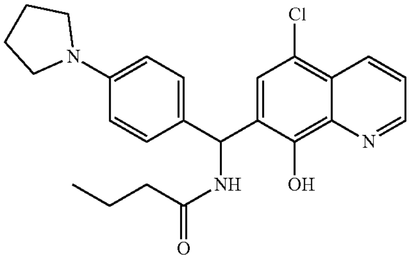,
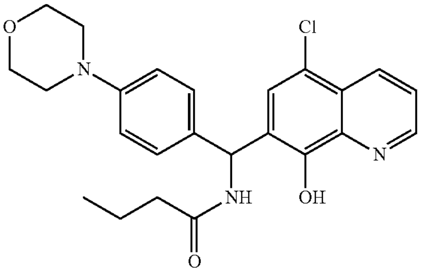,
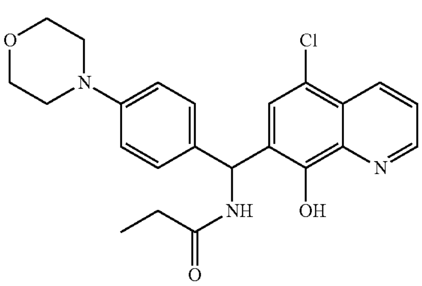, or
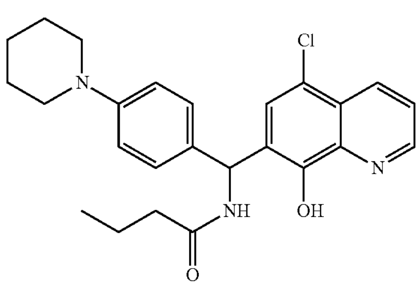.

In one embodiments, the compound is:

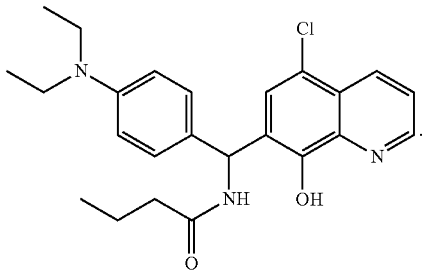 [SMILES: CCCC(=O)NC(c1ccc(N(CC)CC)cc1)c1cc(Cl)c2cccnc2c1O]

Also provided herein, in some embodiments, is a method of treating cancer, the method comprising administering, to a subject in need thereof, one or more compounds selected from the group consisting of compounds having a structure according to Formula I:

I

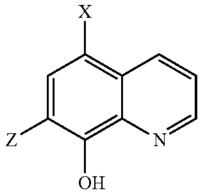

where X is selected from the group consisting of Cl and $NO_2$; and Z is selected from the group consisting of I and H; and compounds having a structure according to Formula II:

II

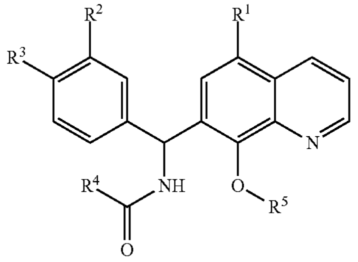

where $R^1$ includes H, Cl, or nitrite; $R^2$ includes H or alkoxy; $R^3$ includes substituted or unsubstituted, branched or unbranched alkyl, alkoxy, amino, halogen, heterocycle, or combinations thereof; $R^4$ includes substituted or unsubstituted, branched or unbranched alkyl; and $R^5$ includes H or methyl carbonyl. In some embodiments of the method, the subject has a cancer that overexpresses KDM3A.

In some embodiments of the method, the compound having a structure according to Formula I includes:

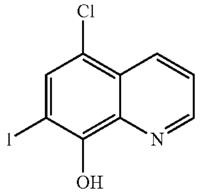
or
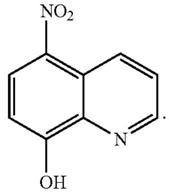

In some embodiments of the method, the compound having a structure according to Formula II includes:

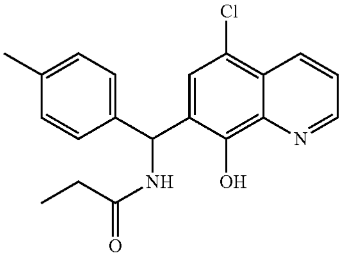
,
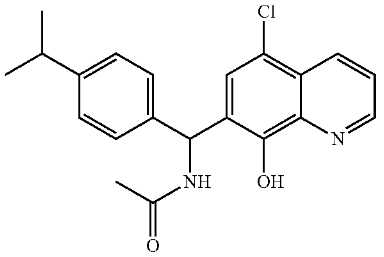
,
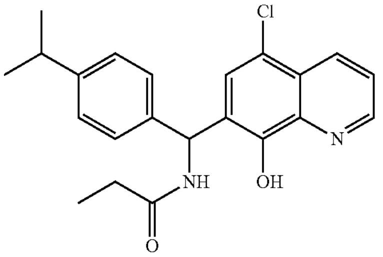
,
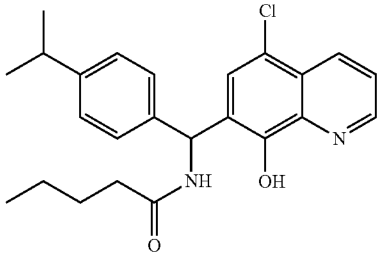
,
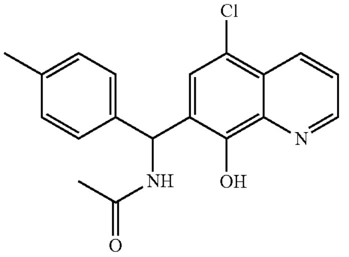
,
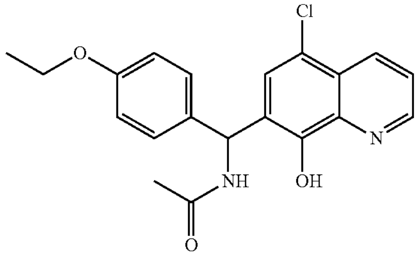
,
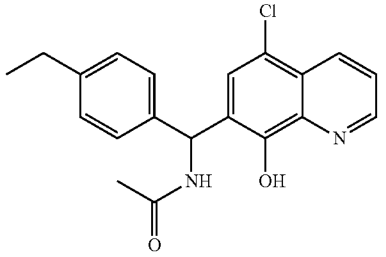
, -continued
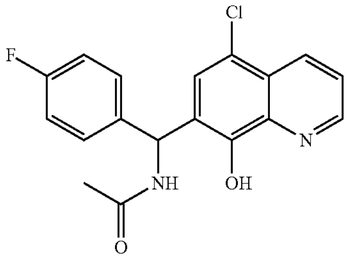
,
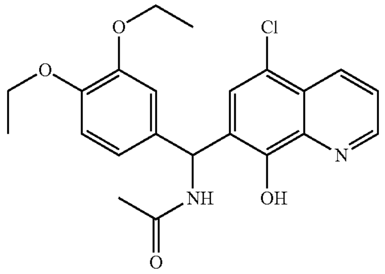
,
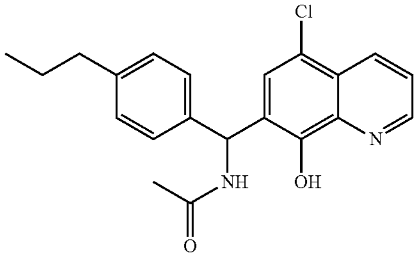
,
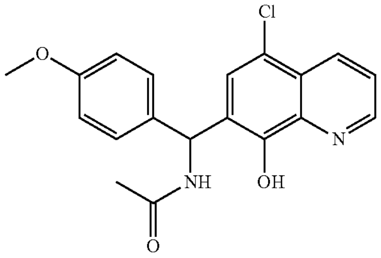
,
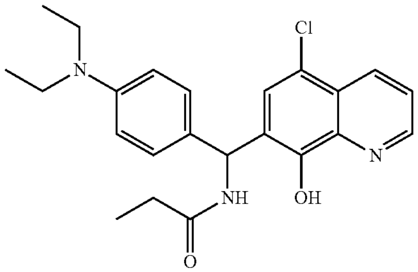
,
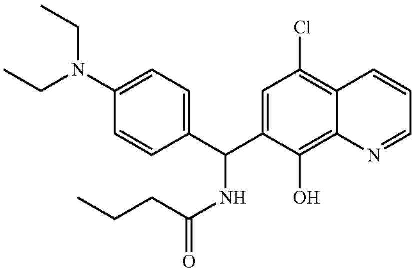
,
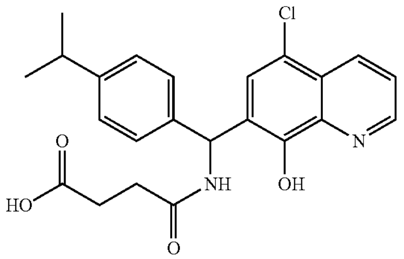
,
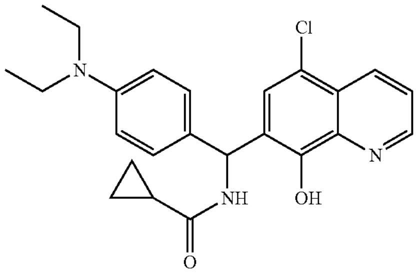
,
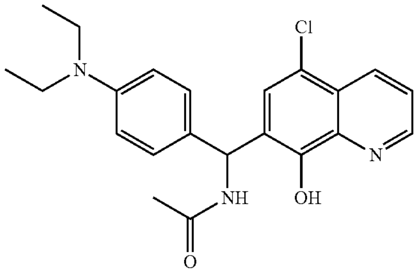
,
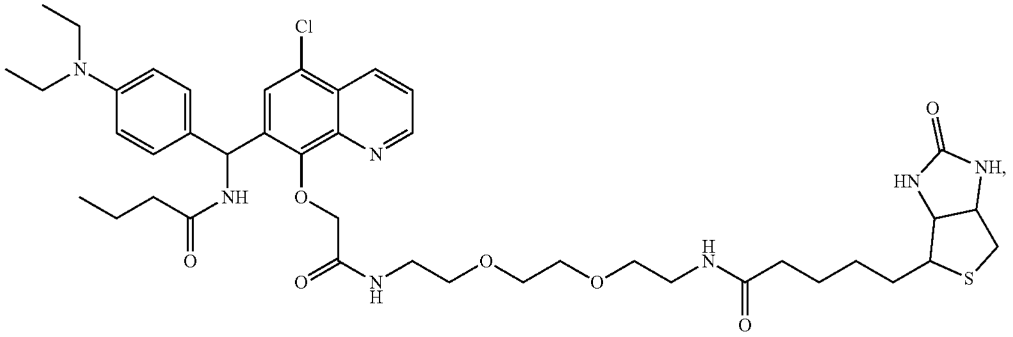

-continued

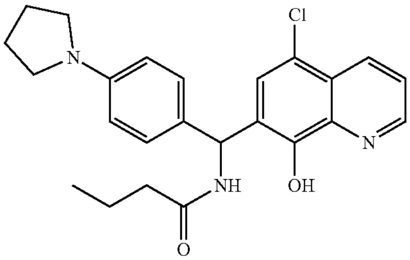
,
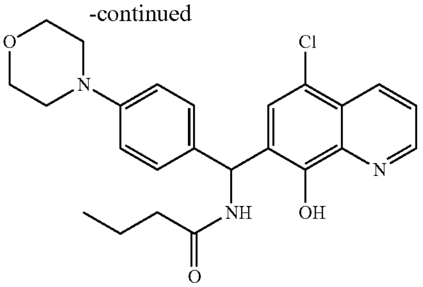
,
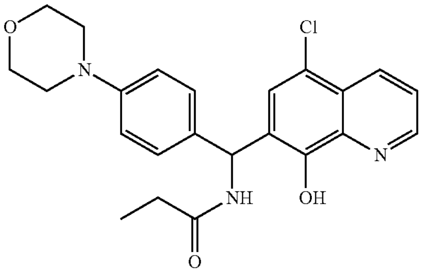
, and
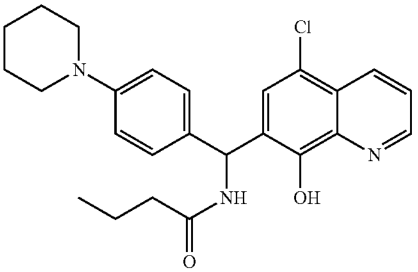
.

In some embodiments of the method, the one or more compounds include:

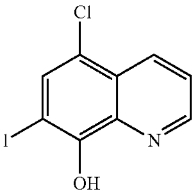
,
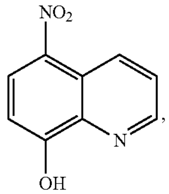
, and
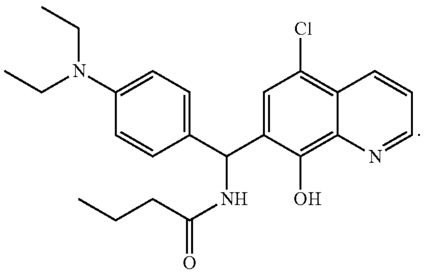
.

Further features and advantages of the presently-disclosed subject matter will become evident to those of ordinary skill in the art after a study of the description, figures, and non-limiting examples in this document.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein:

FIGS. 3A-B show a graph and images illustrating substituted N-benzhydryl-acetamide inhibitors and their effect in luciferase assay. (A) Graph showing the effect of various inhibitors in luciferase assay (“161-0.5” means compound VMS-7-161 at 0.5 μM). (B) Images showing the structures of the inhibitors in A.

Figure 1A:
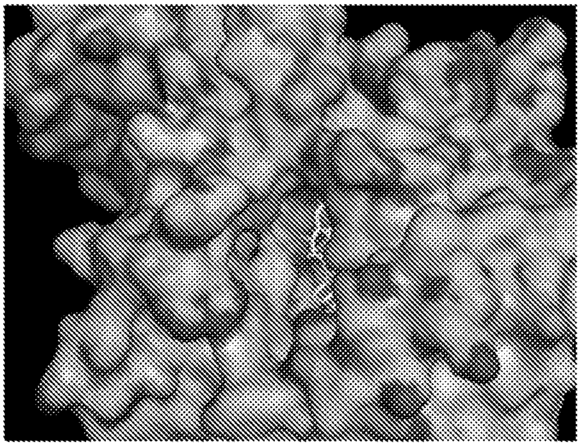
FIGS. 1A-F show a KDM3A inhibitor, called “58B1,” that inhibited Wnt signaling in vitro and in vivo. (A) Docking of 58B1 to the Jumonji domain. (B) 58B1 inhibited KDM3A enzymatic activity in vitro. (C) KDM3A was overexpressed in CRC. (D) 58B1 increased repressor markers, $H3K9Me^2$ and $K3K9Me^3$. (E) 58B1 inhibited Wnt target genes in CRC cells. (F) 58B1 inhibited Wnt signaling in a transgenic zebrafish model. In this model, GFP was control by a Wnt-responsive promoter. In the control fish, GFP was expressed in the tail, where has higher levels on Wnt signaling. 58B1 treatment abolished GFP expression in the tail.
Figure 1B:
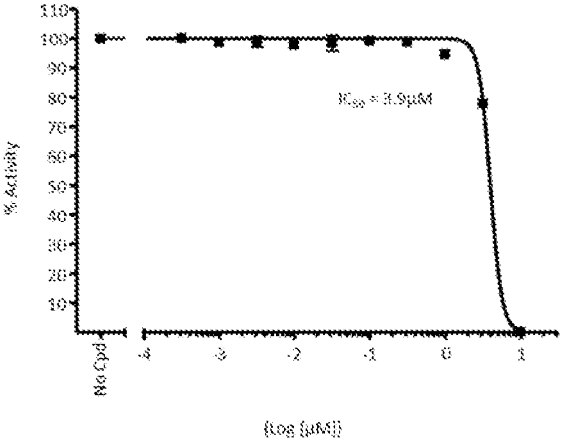
Figure 1C:
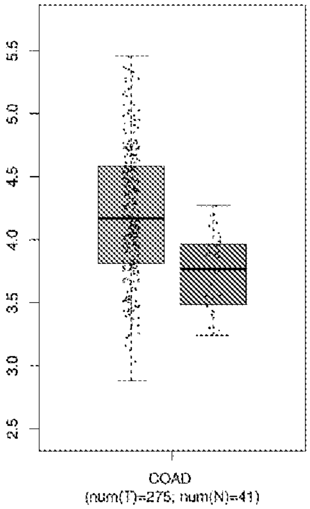

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims, unless the context clearly dictates otherwise. Thus, for example, reference to "a polypeptide" includes one or more of such polypeptides, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Provided herein are compounds for inhibiting Wnt signaling through epigenetic regulation of gene expression. In some embodiments, the compound includes a substituted quinoline having a structure according to Formula I:

I

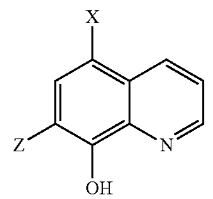

Where X includes Cl or $NO_2$; and Z includes I or H. In some embodiments, the compound includes a substituted N-benzhydryl-acetamide. In some embodiments, the compound includes a substituted benzylquinoline. In some embodiments, the compound includes substituted N-((8-hydroxyquinolin-7-yl)phenylmethyl)amide. In some embodiments, the compound includes any compound having a structure according to Formula II:

II

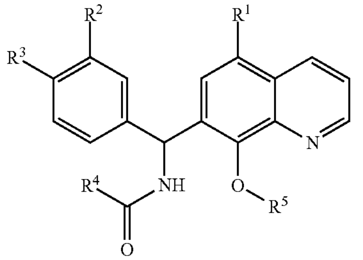

Where $R^1$ includes H, Cl, or nitrite; $R^2$ includes H or alkoxy; $R^3$ is substituted or unsubstituted and includes a branched or unbranched alkyl, alkoxy, amino, halogen, heterocycle (e.g., pyrrolidinyl, piperidinyl, morpholino), or combination thereof; $R^4$ includes a branched or unbranched alkyl, or a substituted branched or unbranched alkyl; and $R^5$ includes H or methyl carbonyl.

In some embodiments, the compound according to Formula I includes the structure where X is Cl and Z is I, or the structure where X is $NO_2$ and Z is H. In some embodiments, the compound according to Formula II includes the structure where $R^1$ is H and $R^2$-$R^5$ are as defined above. In some embodiments, the compound according to Formula II includes the structure where $R^1$ is Cl and $R^2$-$R^5$ are as defined above. In some embodiments, the compound according to Formula II includes the structure where $R^1$ is nitrite and $R^2$-$R^5$ are as defined above. In some embodiments, the compound according to Formula II includes the structure where $R^2$ is H and $R^1$ and $R^3$-$R^5$ are as defined above. In some embodiments, the compound according to Formula II includes the structure where $R^2$ is alkoxy and $R^1$ and $R^3$-$R^5$ are as defined above. In some embodiments, the compound according to Formula II includes the structure where $R^3$ is alkyl and $R^1$-$R^2$ and $R^4$-$R^5$ are as defined above. In some embodiments, the compound according to Formula II includes the structure where $R^3$ is alkoxy and $R^1$-$R^2$ and $R^4$-$R^5$ are as defined above. In some embodiments, the compound according to Formula II includes the structure where $R^3$ is amino and $R^1$-$R^2$ and $R^4$-$R^5$ are as defined above. In some embodiments, the compound according to Formula II includes the structure where $R^3$ is halogen and $R^1$-$R^2$ and $R^4$-$R^5$ are as defined above. In some embodiments, the compound according to Formula II includes the structure where $R^3$ is heterocycle and $R^1$-$R^2$ and $R^4$-$R^5$ are as defined above. In some embodiments, the compound according to Formula II includes the structure where $R^4$ is an unbranched alkyl and $R^1$-$R^3$ and $R^5$ are as defined above. In some embodiments, the compound according to Formula II includes the structure where $R^4$ is an branched alkyl and $R^1$-$R^3$ and $R^5$ are as defined above. In some embodiments, the compound according to Formula II includes the structure where $R^4$ is an unbranched substituted alkyl and $R^1$-$R^3$ and $R^5$ are as defined above. In some embodiments, the compound according to Formula II includes the structure where $R^5$ is H and $R^1$-$R^4$ are as defined above. In some embodiments, the compound according to Formula II includes the structure where $R^5$ is methyl carbonyl and $R^1$-$R^4$ are as defined above.

In some embodiments, the compound according to Formula II includes the structure where $R^1$ is Cl, $R^5$ is H, and $R^2$-$R^4$ are as defined above. In some embodiments, the compound according to Formula II includes the structure where $R^1$ is Cl, $R^5$ is methyl carbonyl, and $R^2$-$R^4$ are as defined above. In some embodiments, the compound according to Formula II includes the structure where $R^1$ is Cl, $R^5$ is H, and $R^2$-$R^4$ are as defined above. In some embodiments, the compound according to Formula II includes the structure where $R^1$ is Cl, $R^2$ and $R^5$ are H, and $R^3$-$R^4$ are as defined above. In some embodiments, the compound according to Formula II includes the structure where $R^1$ is Cl, $R^2$ is alkoxy, $R^5$ is H, and $R^3$-$R^4$ are as defined above. For example, compounds according to Formula I and Formula II include one or more of the following:

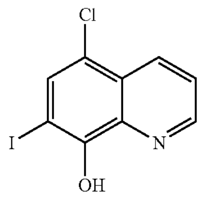

Clioquinol

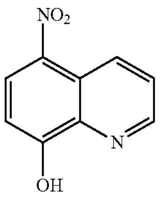

Nitroxoline

VMS-7-79

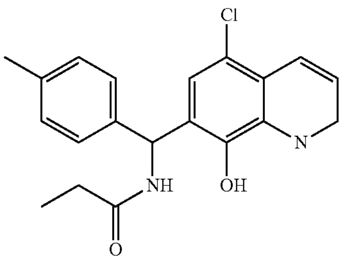

N-((5-chloro-8-hydroxyquinolin-7-yl)(p-tolyl)methyl)propionamine

VMS-7-99

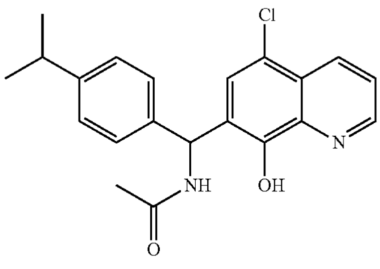

N-((5-chloro-8-hydroxyquinolin-7-yl)(4-isopropylphenyl)methyl)acetamide

-continued

VMS-7-101

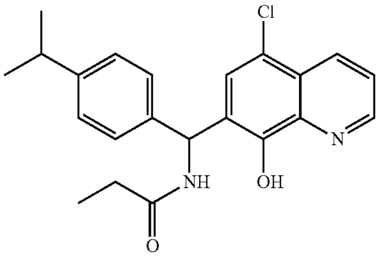

N-((5-chloro-8-hydroxyquinolin-7-yl)(4-isopropylphenyl)methyl)propionamide

VMS-7-105

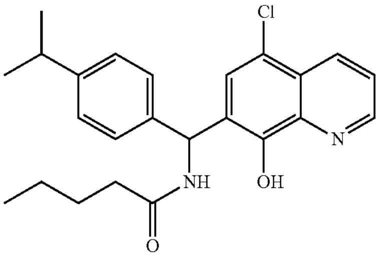

N-((5-chloro-8-hydroxyquinolin-7-yl)(4-isopropylphenyl)methyl)pentanamide

VMS-7-111

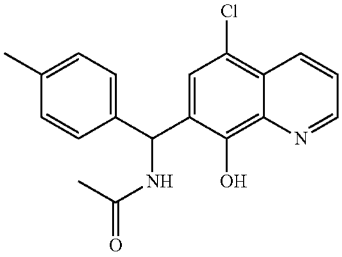

N-((5-chloro-8-hydroxyquinolin-7-yl)(p-tolyl)methyl)acetamide

VMS-7-112

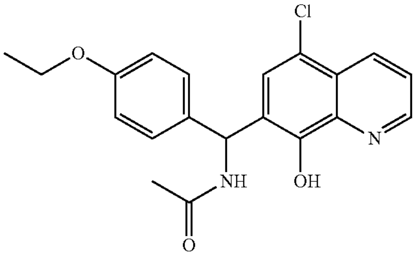

N-((5-chloro-8-hydroxyquinolin-7-yl)(4-ethoxylphenyl)methyl)acetamide

VMS-7-113

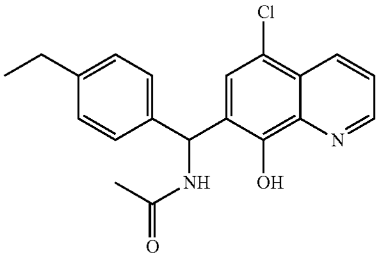

N-((5-chloro-8-hydroxyquinolin-7-yl)(4-ethylphenyl)methyl)acetamide

VMS-7-114

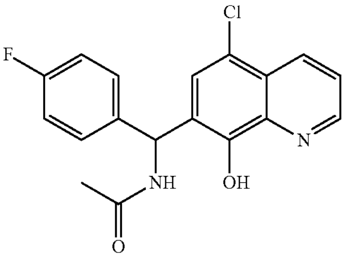

N-((5-chloro-8-hydroxyquinolin-7-yl)(4-fluorophenyl)methyl)acetamide

VMS-7-115

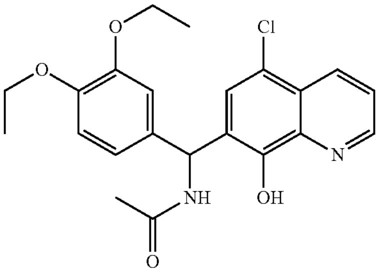

N-((5-chloro-8-hydroxyquinolin-7-yl)(3,4-diethoxyphenyl)methyl)acetamide

VMS-7-116

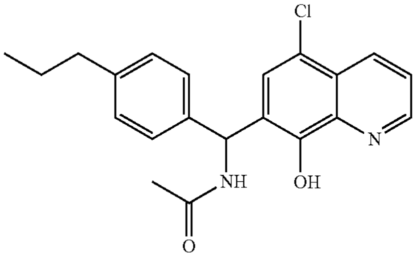

N-((5-chloro-8-hydroxyquinolin-7-yl)(4-propylphenyl)methyl)acetamide

-continued

VMS-7-117

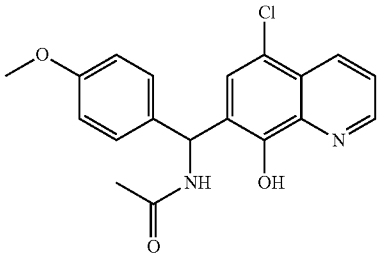

N-((5-chloro-8-hydroxyquinolin-7-yl)
(4-methoxylphenyl)methyl)acetamide

VMS-7-132

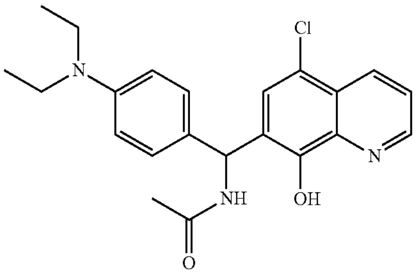

N-((5-chloro-8-hydroxyquinolin-7-yl)
(4-(diethylamino)phenyl)methyl)propionamide

VMS-7-133

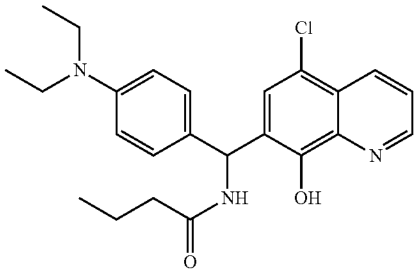

N-((5-chloro-8-hydroxyquinolin-7-yl)
(4-(diethylamino)phenyl)methyl)butyramide

VMS-7-135

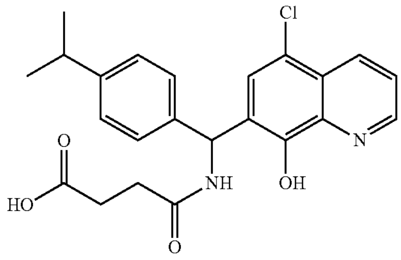

4-(((5-chloro-8-hydroxyquinolin-7-yl)
(4-isopropylphenyl)methyl)amino)-4-oxobutanoic acid

VMS-7-136

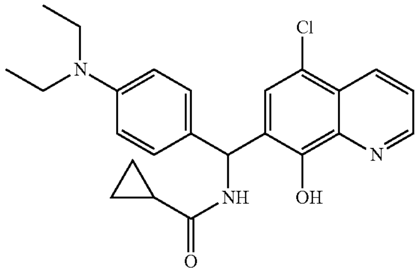

N-((5-chloro-8-hydroxyquinolin-7-yl)
(4-(diethylamino)phenyl)methyl)cyclopropanecarboxamide

VMS-7-139

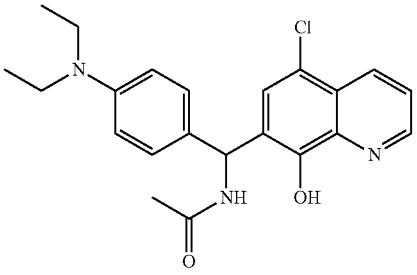

N-((5-chloro-8-hydroxyquinolin-7-yl)
(4-(diethylamino)phenyl)methyl)acetamide

VMS-7-153

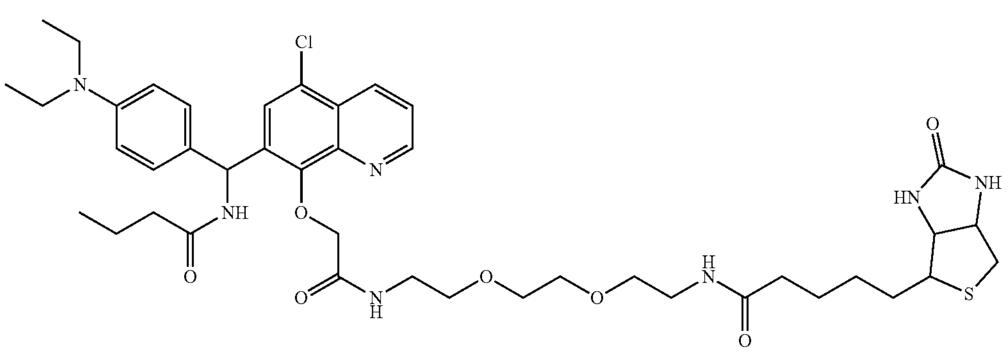

-continued

VMS-7-161

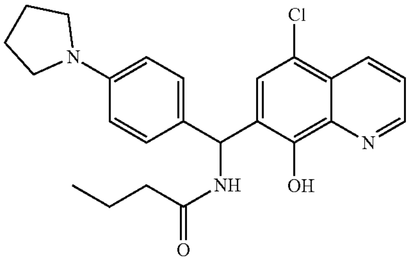

N-((5-chloro-8-hydroxyquinolin-7-yl)(4-(pyrrolidin-1-yl)phenyl)methyl)butyramide

VMS-7-163

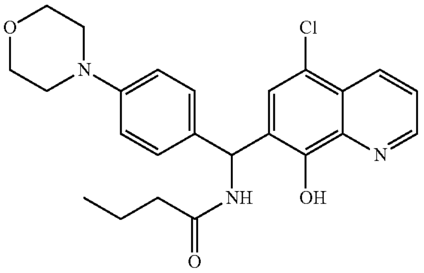

N-((5-chloro-8-hydroxyquinolin-7-yl)(4-morpholinophenyl)methyl)butyramide

VMS-7-164

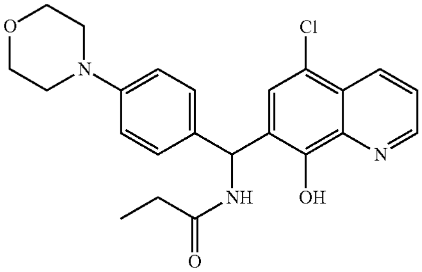

N-((5-chloro-8-hydroxyquinolin-7-yl)(4-morpholinophenyl)methyl)propionamide

VMS-7-165

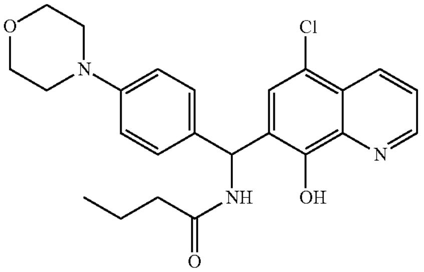

N-((5-chloro-8-hydroxyquinolin-7-yl)(4-(piperidin-1-yl)phenyl)methyl)butyramide

VMS-7-174

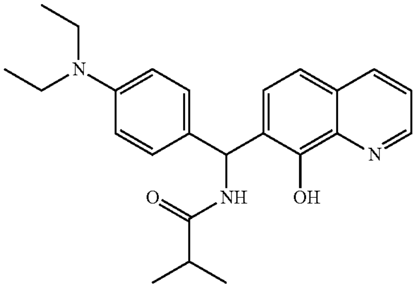

N-((4-diethylamino)phenyl)(8-hydroxyquinolin-7-yl)methyl)isobutyramide

VMS-7-176

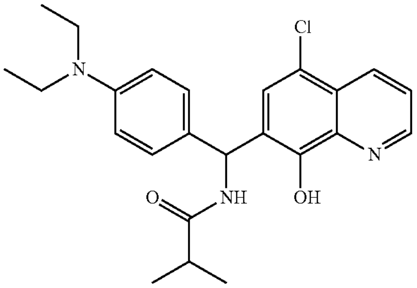

N-((5-chloro-8-hydroxyquinolin-7-yl)(4-diethylamino)phenyl)methyl)isobutyramide

VMS-7-183

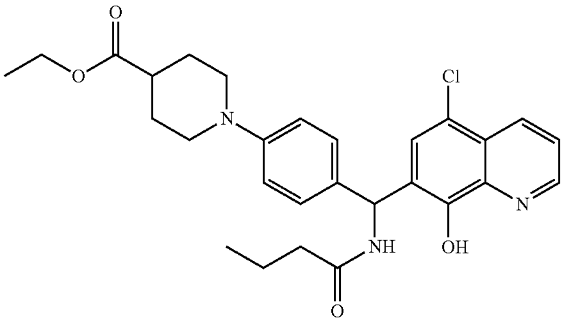

Ethyl 1-(4-(butyramido(5-chloro-8-hydroxyquinolin-7-yl)methyl)phenyl)piperidine-4-carboxylate -continued

VMS-7-193

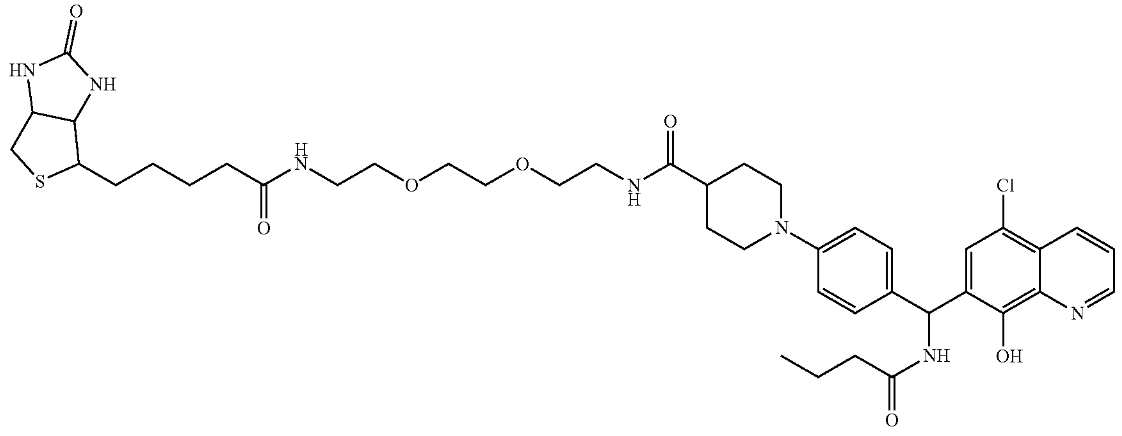

VMS-7-195

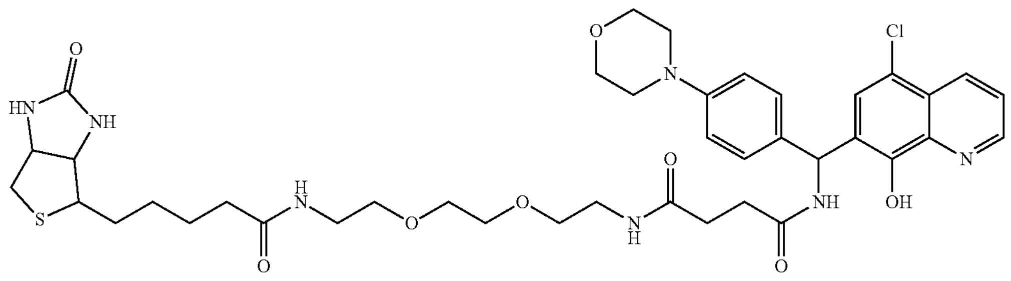

$N^1$-((5-chloro-8-hydroxyquinolin-7-yl)(4-morpholinophenyl)methyl)-$N^4$-(2-(2-(2-(5-(2-oxohexahydro-1H-thieno[3,4-d]imidazole-4-yl)pentanamido)ethoxy)ethyl)succinamide or analogs thereof.

In some embodiments, the compounds disclosed herein inhibit Wnt signaling downstream of β-catenin activity. In some embodiments, the compounds strongly inhibit Wnt target gene expression. For example, in some embodiments, the compounds inhibit Jumanji domain histone demethylases, such as, but not limited to, KDM3A, KDM5B and KDM6A (UTX), resulting in increased H3K9 methylation, which negatively regulates Wnt target gene expression. In some embodiments, one or more of the compounds disclosed herein form novel Wnt inhibitors that function as epigenetic regulators that modulate the frequency, rate, or extent of gene expression in a mitotically or meiotically heritable way without producing a change in the DNA sequence. In some embodiments, one or more of the compounds disclosed herein form novel Wnt inhibitors that selectively target the histone lysine demethylase KDM3A. KDM3A is a Jumanji domain-containing demethylase that regulates the demethylation of histone H3's lysine 9 ($H3K9Me^2$). As such, inhibiting KDM3A increases $H3K9Me^2$ and consequently inhibits Wnt target genes. Accordingly, by inhibiting Wnt signaling downstream of β-catenin activity, the compounds disclosed herein inhibit the proliferation of many cancer cell lines, including cancer cell lines that exhibit overexpression of KDM3A and/or are Wnt signaling activated. Examples of such cancer cell lines include, but are not limited to, CRC, Adenomatous Polyposis Coli (APC)-mutated CRC, CTNNB1 (β-catenin)-mutated CRC, liver cancer, lung cancer, and/or any other cancer where demethylase inhibition provides potential benefits.

Also provided herein are methods of using one or more of the compounds disclosed herein. In some embodiments, the method includes treating cancer with one or more of the compounds disclosed herein. For example, in some embodiments, the method includes administering one or more of the compounds disclosed herein to a subject in need thereof to treat cancer. In some embodiments, the method includes administering one or more of the compounds disclosed herein to a subject having a cancer that overexpresses KDM3A and/or exhibits upregulated KDM3A expression as compared to normal cells of the same tissue. In such embodiments, following administration, the one or more compounds inhibit KDM3A to treat the cancer. For example, in one embodiment, the method includes administering one or more of the compounds disclosed herein to a subject having CRC, which the present inventors found to exhibit significantly upregulated expression levels of KDM3A as compared to normal colon tissues. In another embodiment, the compound includes clioquinol, nitroxoline, and/or VMS-7-133. In another embodiment, the compound includes VMS-7-133.

Additionally or alternatively, in some embodiments, the method includes administering one or more of the compounds disclosed herein to a subject having Wnt signaling activated cancer. In some embodiments, the Wnt signaling activated cancer also exhibits overexpression of KDM3A, which the present inventors have found to reduce histone H3K9 methylation, leading to activation of Wnt signaling. In some embodiments, the cancer includes, but is not limited to, colorectal cancer, liver cancer, lung cancer, and/or any other cancer where demethylase inhibition provides potential benefits. In some embodiments, administering the one or more compounds disclosed herein to a subject in need thereof represents a novel mechanism of action for cancer treatment. Additionally or alternatively, in some embodiments, one or more of the compounds disclosed herein provide greater potency and/or specificity as compared to existing agents.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

Wnt signaling is a key target for multiple human cancers, including but not limited to colon cancer, liver cancer, and lung cancer. To identify novel Wnt regulators by high throughput screening, a stable HEK293T cell line containing the TOPFlash reporter was established. Since β-catenin is often activated by mutations in the Wnt pathway, it is important to inhibit Wnt signaling downstream of β-catenin activity. Therefore, the screen was specifically designed to identify Wnt inhibitors that target events downstream of β-catenin. The Wnt signaling was activated by treating cells with lithium chloride to inhibit GSK3 and to stabilize β-catenin, mimicking the constitutively active Wnt signaling in cancer cells. Through this screen, a family of novel Wnt inhibitors that inhibited Wnt signaling at a 0.5-10 μM concentrations (Table 1) was identified.

The leading compound, 58B1 (plate 58, well B1), was found to strongly inhibit Wnt target gene expression and the proliferation of many cancer cell lines. Mechanically, it was found that 58B1 inhibited Jumanji domain histone demethylases, particularly KDM3A, KDM5B, and KDM6A (UTX). KDM3A is a Jumonji domain-containing demethylase that regulates the demethylation of histone H3's lysine 9 ($H3K9Me^2$). Inhibiting KDM3A increased $H3K9Me^2$, which increased H3K9 methylation and consequently inhibited Wnt target genes. When evaluated in connection with CRC cells, which were found to exhibit significantly upregulated KDM3A, 58B1 inhibited CRC cell proliferation at 100 nM concentration. Inhibiting KDM3A also inhibited Wnt signaling in an in vivo Zebrafish model.

To study the structure and activity relationship (SAR) and to improve the activity of these compounds, a panel of 58B1 analogs was synthesized and additional active Wnt inhibitors were identified. These compounds are potent, specific KDM inhibitors that may be used for cancer treatment.

TABLE 1

Structures of substituted N-benzhydryl-acetamide inhibitors and percent inhibition of proliferation of colorectal cancer cells.

| Name | Structure | Inhibition (%) |
|---|---|---|
| 58B1 | 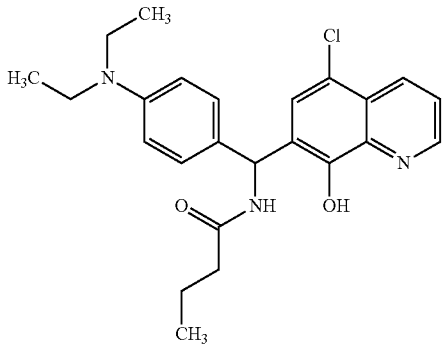 [SMILES: CCCC(=O)NC(c1ccc(N(CC)CC)cc1)c1cc(Cl)c2cccnc2c1O] | 95 |
| 58D8 | 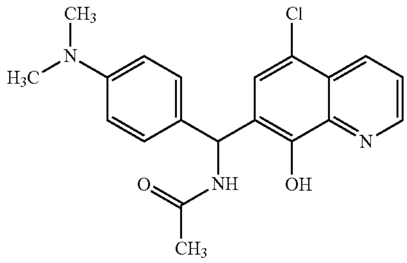 [SMILES: CC(=O)NC(c1ccc(N(C)C)cc1)c1cc(Cl)c2cccnc2c1O] | 90 |
| 58F8 | 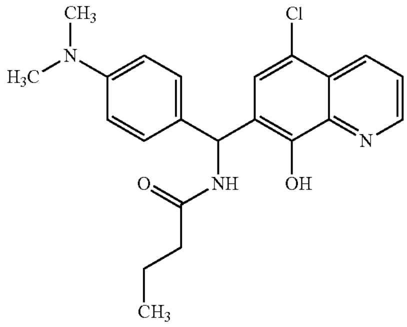 [SMILES: CCCC(=O)NC(c1ccc(N(C)C)cc1)c1cc(Cl)c2cccnc2c1O] | 88 |
| 48M1 | 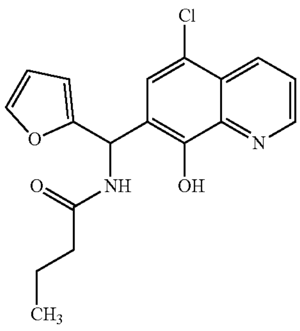 [SMILES: CCCC(=O)NC(c1ccco1)c1cc(Cl)c2cccnc2c1O] | 82 |

TABLE 1-continued

Structures of substituted N-benzhydryl-acetamide inhibitors and percent inhibition of proliferation of colorectal cancer cells.

| Name | Structure | Inhibition (%) |
|---|---|---|
| 58H8 | 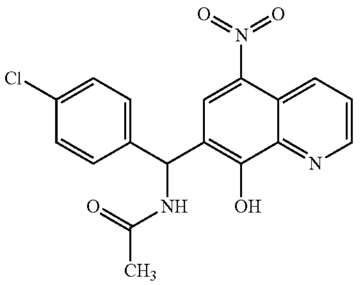 [SMILES: CC(=O)NC(c1ccc(Cl)cc1)c1cc([N+](=O)[O-])c2cccnc2c1O] | 80 |
| 58B6 | 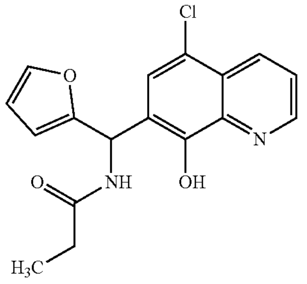 [SMILES: CCC(=O)NC(c1ccco1)c1cc(Cl)c2cccnc2c1O] | 73 |

TOPFlash Reporter Assay

Stable HEK293T cell line transfected with a TOPFlash plasmid was treated with DMSO or 2.5 mM of each compound. After 6 h, the cells were treated with 25 mM LiCl to activate Wnt signaling. The inhibition ratio of each compound was determined (Table 1).

Effects of 58B1 on Wnt Target Genes in Colon Cancer Cells

The activities of 58B1 were validated by western blotting. 58B1 (5 μM) strongly inhibited the expression Wnt target genes in LS174T colon cancer cells (FIGS. 1A-F).

Effects on Colon Cancer Cell Proliferation

Figure 2:
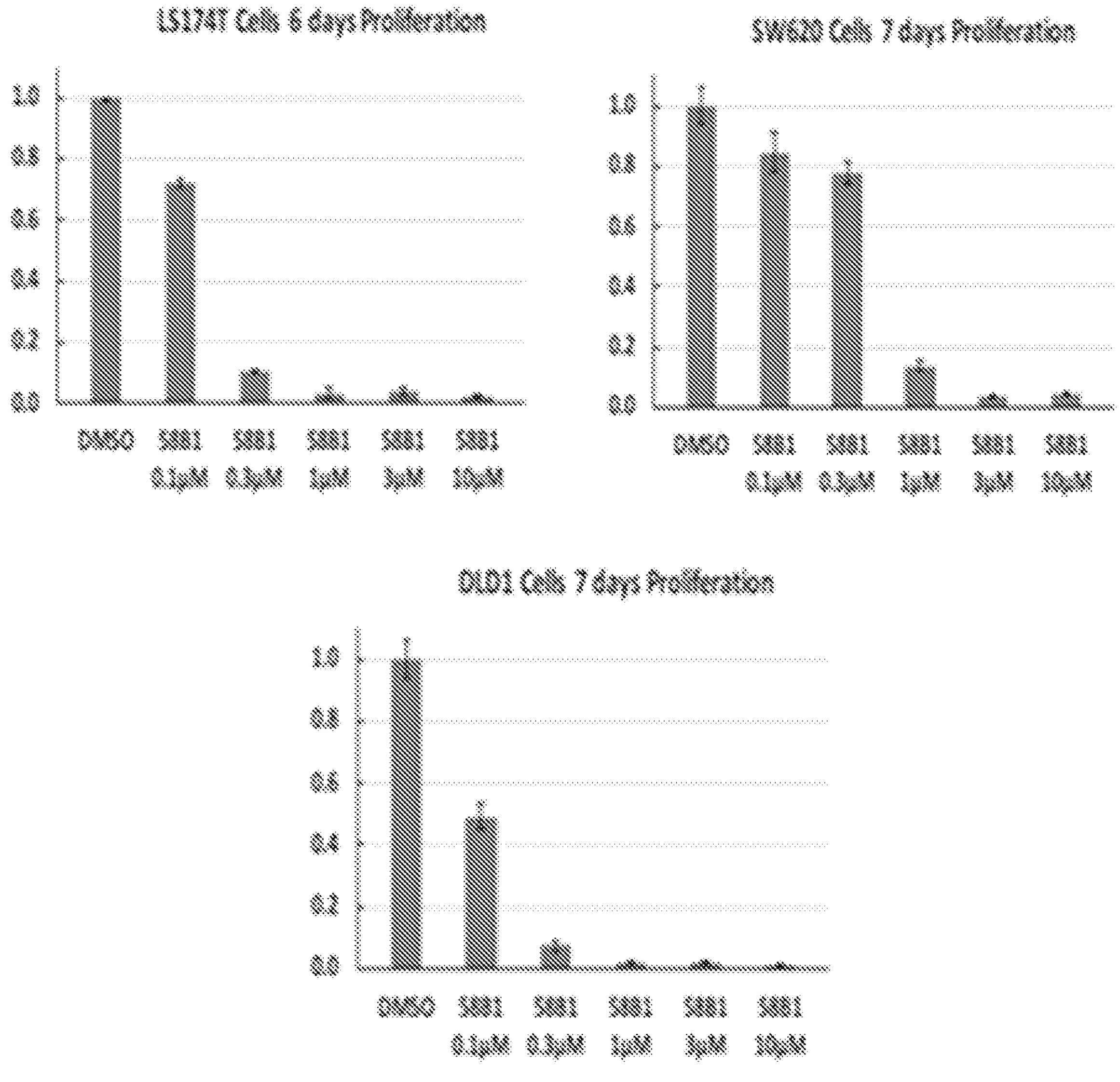
FIG. 2 shows graphs illustrating the effects of inhibitors on proliferation of colon cancer cell line LS174T.

The effects of these compounds on proliferation of colon cancer cell line LS174T and DLD1 were analyzed. 58B1 strongly inhibited the proliferation of these cancer cells at low nanomolar concentrations (FIG. 2).

Mechanism Studies

Figure 1D:
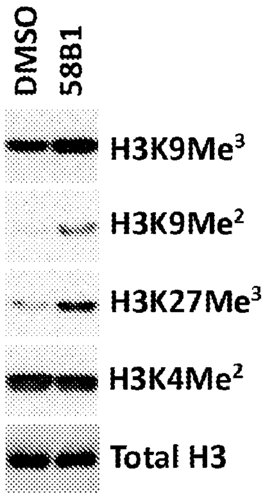
Figure 1E:
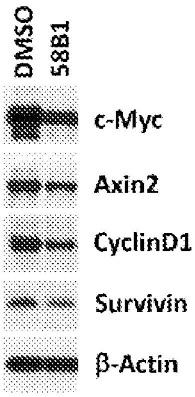
Figure 1F:
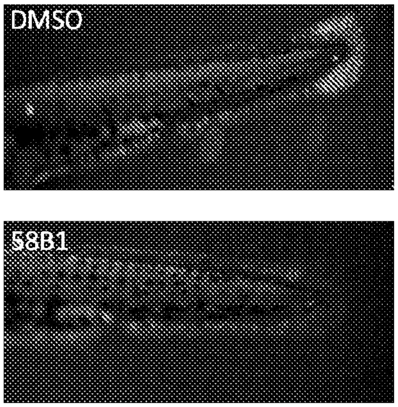

To determine if 58B1 regulates Wnt signaling through epigenetic mechanism, the effects of 58B1 on histone methylation were analyzed. It was found that 58B1 (5 μM) strongly induced H3K9 dimethylation ($H3K9Me^2$) in HEK293T cells (FIG. 1D). It also induced $H3K9Me^3$ and $H3K27Me^3$ but not $H3K4me^2$. Similar results were found in LS174T colon cancer cells. H3K9 and H3K27 methylations are negative regulators of transcription. Without wishing to be bound by theory, it is believed that 58B1 inhibited Wnt signaling by increasing H3K9 or H3K27 methylation on Wnt target gene promotors.

Histone Demethylase Assay

To further examine the effects of 58B1 on histone demethylase, we screened a panel of purified histone demethylases was screened. 58B1 inhibited Jumanji domain KDMs, such as JMJD1A (KDM3A), JMJD2A (KDM4A), JMJD2C (KDM4C), Jarid1B (KDM5B), UTX (KDM6A) and JMJD3 (KDM6B), but was less effective for other type of KDMs, such LSD1 (KDM1A) and FBXL10 (KDM2B) (Table 2).

TABLE 2

Effects of 58B1 on histone demethylases.

| | % Inhibition | |
|---|---|---|
| Enzymes | 58B1,10 μM | Reference |
| JMJD2A | 64 | 100<br>2,4-Pyridine Dicarboxylic Acid |
| JMJD2C | 72 | 100<br>2,4-Pyridine Dicarboxylic Acid |
| JMJD3 | 94 | 100<br>GSK-J1 |
| JMJD1A | 99 | 100<br>JIB-04 |
| LSD1 | 32 | 100<br>GSK-LSD1 |
| Jarid1B | 95 | 100<br>GSK-J1 |
| FBXL10 | 30 | 99<br>2,4-Pyridine Dicarboxylic Acid |
| UTX | 100 | 100<br>GSK-J1 |

SAR Studies

Figure 3A:
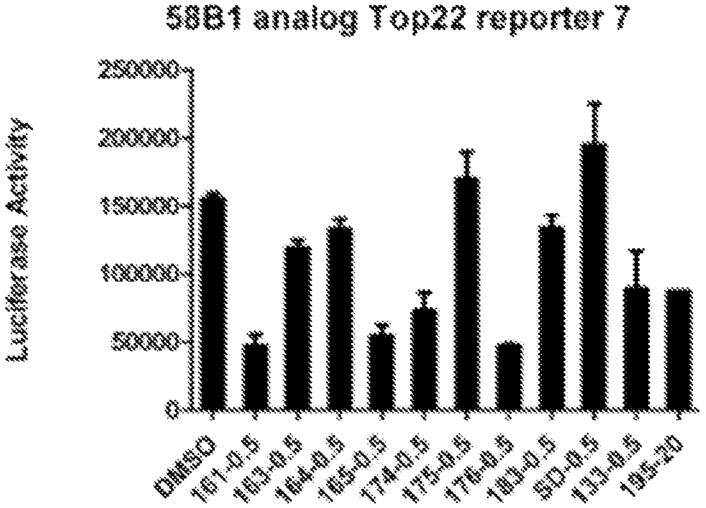

For the SAR studies, 58B1 (VMS-7-133) was re-synthesized. Additionally, SD70, a commercial KDM4 inhibitor, was both purchased and re-synthesized (VMS-7-175). These compounds were compared using Wnt reporter assay at 1 μM (Table 3) and then the most active compounds were compared at 0.5 μM (FIGS. 3A-B). VMS-7-195 is a biotinylated analog of 58B1. From the SAR study, more active 58B1 analogs for Wnt inhibition have been identified. Specific KDM inhibitors may be used to target specific KDMs, such as KDM3A, which is highly expressed in many human cancers.

TABLE 3

Percent inhibition of substituted N-benzhydryl-acetamide inhibitors at 1 μM concetrations.

| | | |
|---|---|---|
| VMS-7-79 | $C_{20}H_{19}ClN_2O_2$ | 13.7 |
| VMS-7-99 | $C_{21}H_{21}ClN_2O_2$ | 41.1 |
| VMS-7-101 | $C_{22}H_{23}ClN_2O_2$ | 73.3 |
| VMS-7-105 | $C_{24}H_{27}ClN_2O_2$ | 38.7 |
| VMS-7-111 | $C_{19}H_{17}ClN_2O_2$ | 28.3 |
| VMS-7-112 | $C_{20}H_{19}ClN_2O_3$ | 68.5 |
| VMS-7-113 | $C_{20}H_{19}ClN_2O_2$ | 30.6 |
| VMS-7-114 | $C_{18}H_{14}ClFN_2O_2$ | 55.5 |
| VMS-7-115 | $C_{22}H_{23}ClN_2O_4$ | 44.3 |
| VMS-7-116 | $C_{21}H_{21}ClN_2O_2$ | 68.1 |
| VMS-7-117 | $C_{19}H_{17}ClN_2O_3$ | 43.5 |
| VMS-7-118 | $C_{29}H_{25}Cl_2N_3O_2$ | 69.4 |
| VMS-7-102 | $C_{28}H_{22}Cl_2N_2O_2$ | 55.1 |
| VMS-7-133 | $C_{24}H_{28}ClN_3O_2$ | 90.9 |
| VMS-7-132 | $C_{23}H_{26}ClN_3O_2$ | 84.6 |
| VMS-7-139 | $C_{22}H_{24}ClN_3O_2$ | 30.6 |
| VMS-7-136 | $C_{24}H_{26}ClN_3O_2$ | 89.3 |
| VMS-7-135 | $C_{23}H_{23}ClN_2O_4$ | 7.7 |
| SD70 | $C_{18}H_{18}N_2O_3$ | 53.8 |
| VMS-7-175 | $C_{18}H_{18}N_2O_3$ | 49.7 |
| VMS-7-174 | $C_{24}H_{29}N_3O_2$ | 97.5 |
| VMS-7-176 | $C_{24}H_{28}ClN_3O_2$ | 98.2 |
| VMS-7-161 | $C_{24}H_{26}ClN_3O_2$ | 99.7 |
| VMS-7-165 | $C_{25}H_{28}ClN_3O_2$ | 95.2 |
| VMS-7-183 | $C_{28}H_{32}ClN_3O_4$ | 85.6 |
| VMS-7-163 | $C_{24}H_{26}ClN_3O_3$ | 93.2 |
| VMS-7-164 | $C_{23}H_{24}ClN_3O_3$ | 93.4 |

Example 2—JmjC Domain-Containing Histone Demethylase Inhibitors for Colon Cancer Treatment CRC is the second leading cause of cancer-related mortality in the United States. One hallmark of CRC associated with disease progression and metastasis is over-activation of the Wnt signaling pathway. A majority of CRC cases involve mutations in the Wnt signaling pathway, primarily in either the Adenomatous Polyposis Coli (APC) gene or the CTNNB1 (β-catenin) gene. These mutations increase the levels of β-catenin, a transcriptional co-activator that controls the expression of many important genes in tumorigenesis. In normal cells, β-catenin undergoes phosphorylation by CK1α and GSK3 and degradation through β-TrCP-mediated ubiquitination. In CRC cells, the APC and β-catenin mutations prevent not only this normal β-catenin phosphorylation and ubiquitination but also promote abnormal β-catenin stabilization and nuclear accumulation. In the nucleus, β-catenin binds TCF/LEF and its co-activators, such as CBP/p300, and activates the transcription of Wnt target genes, including many oncogenes.

The crucial role played by Wnt signaling in CRC progression makes it a challenging but valid target for the development of new antineoplastic agents. Previous efforts along these lines, however, target upstream events in the Wnt signaling pathway to induce β-catenin degradation. For example, a tankyrase inhibitor, XAV939, stabilizes Axin and induces β-catenin degradation. Porcupine (PORCN) inhibitors, IWP2 and LSK-974, inhibit Wnt processing and secretion. These agents may inhibit Wnt signaling in normal cells; but, unfortunately, are ineffectual for CRC cells containing Wnt pathway mutations. As such, despite decades of research and clinical studies, no FDA-approved clinical agents targeting this pathway are available. Thus, it is imperative to develop Wnt inhibitors targeting key steps that lie downstream of β-catenin.

Recognizing this need, others developed Wnt inhibitors to inhibit the β-catenin/TCF, the β-catenin/Bcl9, and the β-catenin/CBP interactions, and the present inventors recently found that Wnt signaling can be inhibited by reducing ATP levels required for chromatin remodeling. Histone methylation events on various lysine residues may either activate or repress transcription. The generation of $H3K4Me_3$ by MLL1/2/ASH2L histone lysine methyltransferase complexes (KMTs) activates Wnt signaling. On the other hand, histone demethylases (KDMs) also regulate histone methylation events and thereby affect chromatin remodeling and gene expression. Inhibition of KDMs may lead to a net increase in histone methylation at specific lysine residues, leading, for example, to increased methylation of H3K9 or H3K27 that in turn would repress transcription. The first reported KDM is LSD1 that belongs to the so-called "type 1" family of KDMs that contain a flavin adenine dinucleotide (FAD)-dependent amine oxidase. The second type of KDMs contains a Jumonji C (JmjC)-domain and includes seven families of human JmjC-domain containing KDMs with specific demethylase activities.

This Examples discusses the development of novel epigenetic Wnt inhibitors that either inhibit active histone marking or induce repressive histone marking on Wnt target genes. More specifically, this Example discusses development of KDM inhibitors in the carboxamide-substituted benzhydryl amine (CBA) family that not only elucidate the molecular mechanisms by which specific KDMs regulates Wnt signaling but also provide new drug targets and new drug candidates for CRC treatment. In the course of developing these new Wnt inhibitors, CBA-1 (also referred to herein as VMS-7-133) was identified as an epigenetic regulator that inhibits KDMs possessing the Jumanji C (JmjC) domain, restores the repressive histone methylation marks, and inhibits Wnt signaling in CRC. Small-molecule inhibitors like CBA-1 function as epigenetic Wnt inhibitors for specific histone demethylases, particularly, KDM3A. KDM3A up-regulation activates Wnt signaling by reducing the repressive H3K9 methylation of Wnt target genes. Specific inhibition of KDM3A represses Wnt signaling and this inhibition represents a new paradigm in treating tumors with activating mutations in the Wnt pathway. Based on SAR and molecular docking studies, CBA-1 analogs from antibiotics were also identified, as potential "repurposed" KDM3 inhibitors, which showed promising activities in repressing CRC xenografts in mouse models.

Figure 4:
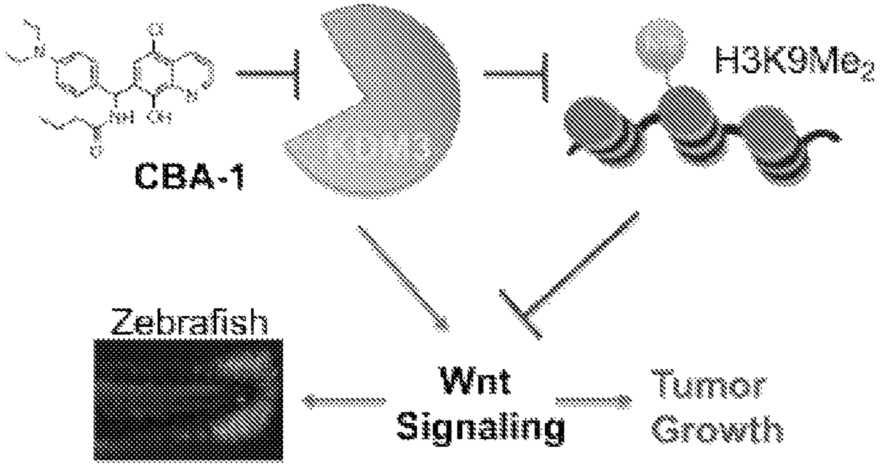
FIG. 4 shows a schematic illustrating that CBA-1 (also referred to herein as 58B1 and VMS-7-133) is an epigenetic inhibitor for Wnt signaling in CRC.

Delineate the mechanisms of CBA-1 in Wnt signaling and CRC inhibition. The present inventors have identified CBA-1 (FIG. 4) as an epigenetic Wnt inhibitor that depressed Wnt signaling in CRC cells and Zebrafish models. Additionally, KDM3A has been identified as a major target for CBA-1 using a biotinylated, biologically active derivative, and it was confirmed that KDM3A was required for Wnt signaling in CRC cells.

Figure 5A:
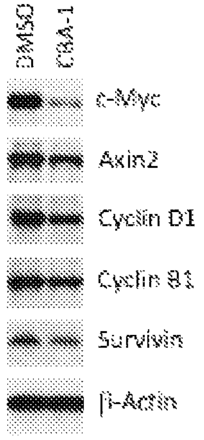
FIGS. 5A-B show an image and graph illustrating validation of CBA-1. (A) CBA-1 repressed Wnt targets in LS174T CRC cells. (B) CBA-1 inhibited CRC cell proliferation (5d, Vi-Cell viability assay).
Figure 5B:
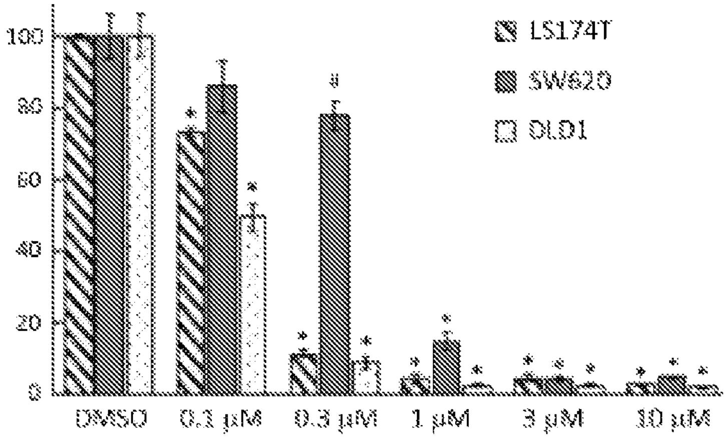

Identification of a CBA-1 as a novel Wnt inhibitor. The present inventors routinely use TOPFlash reporter assay for Wnt inhibitor screening. To mimic the constitutively active Wnt signaling found in CRC cells, Wnt signaling was activated by inhibiting GSK3 and stabilizing β-catenin. From screening in house small-molecule libraries, CBA-1 (FIG. 4) was identified that inhibited Wnt signaling in TOPFlash reporter assay. To validate the screening results, CBA-1 was tested in CRC cells. Treatment of CRC cells with CBA-1 repressed the expression of Wnt target genes (FIG. 5A) and inhibited proliferation of CRC cell lines with APC (SW620 and DLD1) or β-catenin (LS174T) mutations (FIG. 5B).

Figure 6A:
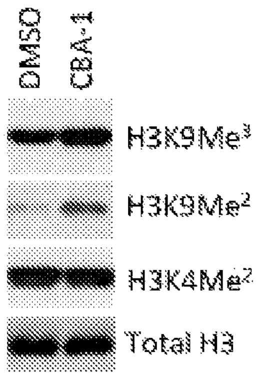
FIGS. 6A-B show images illustrating that CBA-1 regulates histone methylation. (A) CBA-1 increase total $H3K9Me^2$ levels. (B) CBA-1 increased $H3K9Me^2$ levels on c-myc promoter.
Figure 6B:
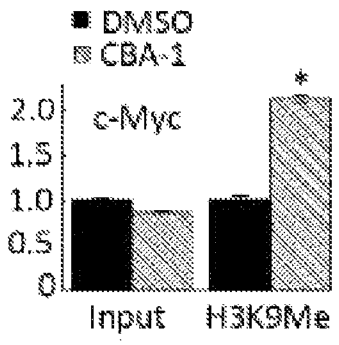

CBA-1 increased repressive histone methylation on Wnt target genes. The present inventors reported that mutations in APC or β-catenin N-terminal phosphorylation sites prevented β-catenin degradation in CRC cells. For example, LS174T cells possess β-catenin mutation at Ser45, and DLD-1 cells contain an APC truncation. Because CBA-1 inhibited Wnt signaling in CRC cells, it was reasonable to assume that it inhibited Wnt signaling downstream of β-catenin, most likely by blocking β-catenin activity in the nucleus. Consequently, the present inventors hypothesized that CBA-1 inhibited Wnt signaling epigenetically by altering chromatin remodeling, and they probed the effects of CBA-1 on histone methylation in CRC cells. CBA-1 significantly increased the levels of $H3K9Me^2$ and $H3K9Me^3$ but had no effect on $H3K4Me^2$ (FIG. 6A). These outcomes suggested that CBA-1 inhibited specific KDM(s) and thereby promoted increased methylation levels of histones and ultimately inhibited transcription. Indeed, chromatin immunoprecipitation (ChIP) assay followed by qPCR found that CBA-1 increased the levels of H3K9Me2 on the promoter of c-Myc gene (FIG. 6B).

Figure 7A:
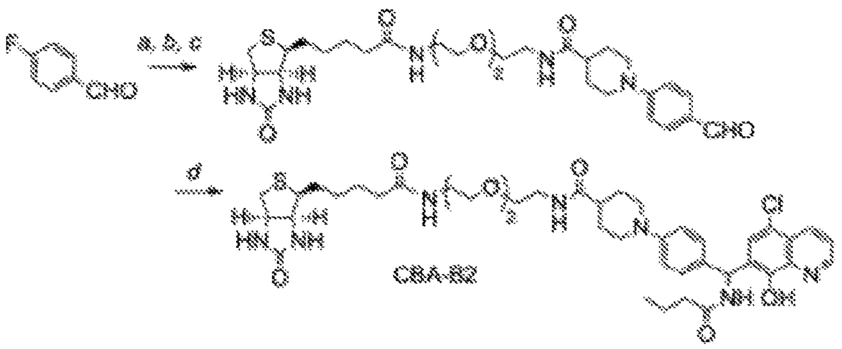
FIGS. 7A-E show images and a graph illustrating that CBA-1 interacts with KDM3A. (A) CBA-B2, a biotinylated CBA. (B) KDM3A was pulled down from HEK293T cell lysates by CBA-B2 and streptavidin beads. (C) CBA-1 inhibited the enzymatic activities of KDM3A. (D) Knocking down of KDM3 inhibited LS174T cell proliferation. (E) Knocking down of KDM3 reduced Wnt target genes expression.
Figure 7B:
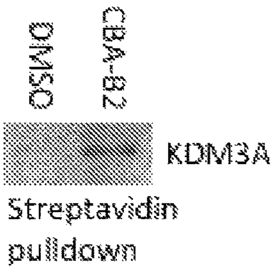
Figure 7C:
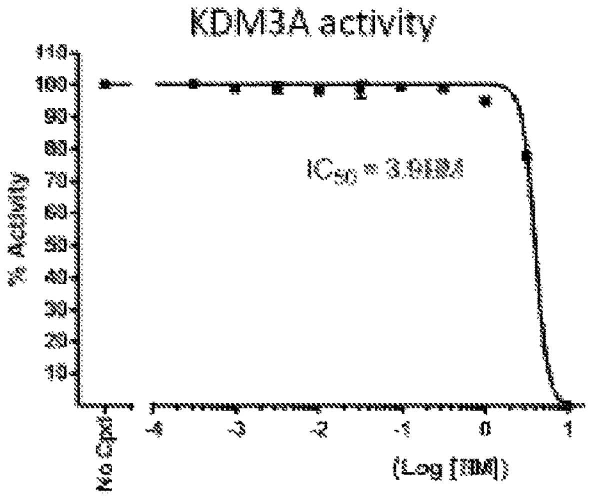
Figure 7D:
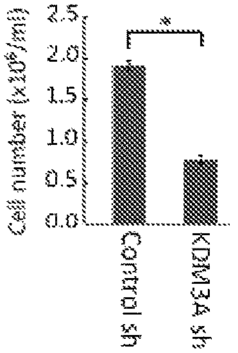
Figure 7E:
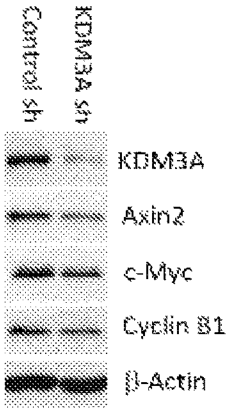

Identification of KDM3A as a target of CBA-1. KDM3A regulated $H3K9Me^2$ and underwent significant upregulation in CRC. To test if CBA-1 targeted KDM3A, a biotinylated analog CBA-B2 (FIG. 7A) was synthesized. It was determined that CBA-B2 retained sufficient Wnt inhibition activity. Streptavidin beads/CBA-B2 pull-down studies suggested that CBAs bound endogenous KDM3A (FIG. 7B). Consistent with this binding result, a dose-response study suggested that CBA-1 inhibited KDM3A activity in vitro at low micromolar levels (FIG. 7C). Knocking-down KDM3A by shRNA inhibited cell proliferation (FIG. 7D) and Wnt target gene expression in LS174T CRC cells (FIG. 7E). These studies corroborated the CBA-1 inhibition of KDM3A as the key event in the observed Wnt inhibition and CRC cell growth inhibition and suggested that KDM3A was a promising target for drug intervention for CRC.

Figure 8A:
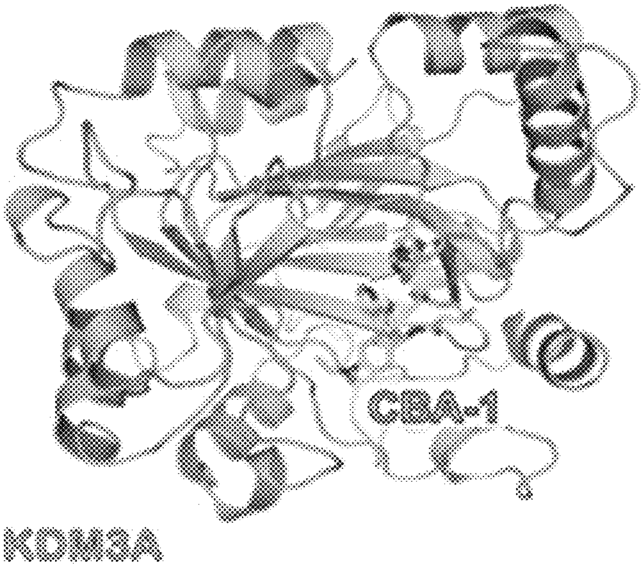
FIGS. 8A-B shows images illustrating molecular modeling of the binding site of KDM3A with CBA-1. (A) Global view of the binding of CBA-1 to KDM3A. Cartoon model representations are shown of the KDM3A in cyan. CBA-1 is shown in stick model and colored yellow. (B) Local view of the $Mn^{2+}$ binding site including CBA-1. Residues involved in the binding site are shown with stick model and colored the same color as its protein backbone. Dashed lines represent the coordination with distances shown close to the respective lines.

Molecular modeling. KDM3A exhibited 89% sequence similarity and 60% sequence identity to another family member, KDM3B, that possessed a JmjC domain and a reported, high-resolution crystal structure (PDB: 4C8D). Molecular dynamics were utilized to construct a reasonable representation of KDM3A using the structure of KDM3B as a departure point. According to the RCSB database, the coordination of the manganese ion ($Mn^{2+}$) in the KDM3B active site involved water and N-oxalylglycine, and similar coordination was assumed in the modeled structure for KDM3A. In the homology model of KDM3A that emerged from these studies, the binding pose of the modeled structure of KDM3A (FIG. 8A) predicted that CBA-1 coordinated directly to the $Mn^{2+}$ ion site. An expanded view (FIG. 8B) of the coordination of $Mn^{2+}$ by CBA-1 showed that nitrogen of the quinoline ring in CBA-1 coordinated with the $Mn^{2+}$ at 2.8 Å. The carboxamide group of KDM3A (D1122) also coordinated with $Mn^{2+}$ at 2.1 Å. Interesting hydrophobic interactions were noted between portions of CBA-1 and residues L1121, V1123, and F1280 that resided within 4 Å of CBA-1. Finally, various polar and charged residues surrounded CBA-1 within 3 Å and defined the arrangement of functional groups in CBA-1 that provided the specificity seen in its binding to KMD3A. The docking of other published KDM inhibitors, such as JMJD3/UTX inhibitor GSK-J1, was also analyzed and CBA-1 was superior as a KDM3A inhibitor based on calculated, binding free energies and Wnt inhibition experiments.

Figure 9:
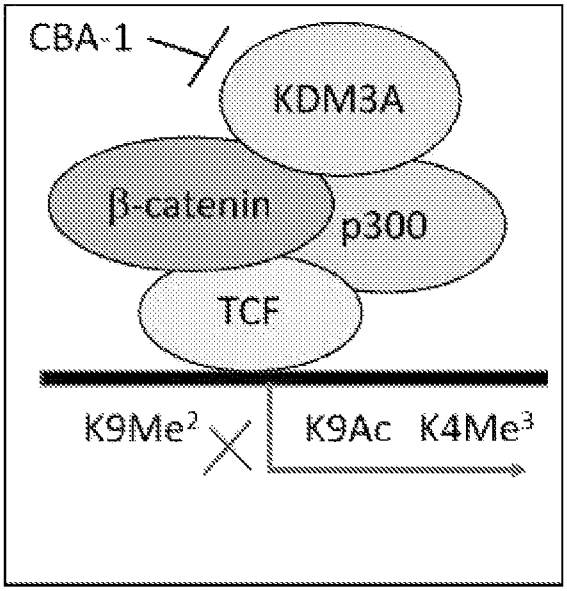
FIG. 9 shows a schematic illustrating potential mechanisms of CBA-1 in Wnt inhibition.

Effects of CBA-1 on β-catenin complex. In CRC cells, stabilized b-catenin binds TCF/LEF on Wnt-target promoters, recruiting co-activators, p300, for histone acetylation, and Ash2L/MLL for $H3K4Me^3$ methylation (FIG. 9). It has been reported that KDM3A may interact with both b-catenin and p300. The present inventors found that CBA-1 inhibited Wnt/β-catenin signaling by targeting KMD3A and reducing $H3K9Me^2$ on Wnt target promoters.

Interaction of CBA-1 with KDM3A. Molecular docking of CBA-1 to KDM3A revealed three interactions that determine the specificity and high affinity of CBA-1 to KDM3A. The nitrogen in the CBA-1 quinoline interacts with the cofactor, $Mn^{2+}$, in KDM3A. Related isoquinolines are inactive at levels below 10 μM. KDM3A residues, D1122, H1249 and H1120 also coordinate with $Mn^{2+}$. CBA-1 also has a hydrophobic interaction with other KDM3A residues. In addition, there are a number of charged residues in KDM3A that define the pose of CBA-1. In contrast, the GSK-J1 inhibitor of KDM6 only interacted with $Mn^{2+}$ but not with hydrophobic and charged residues.

Figure 8B:
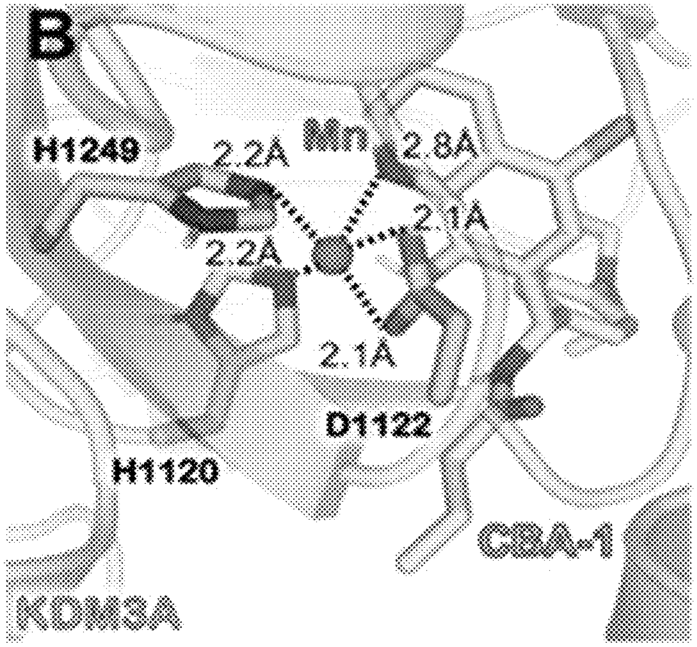
Figure 10A:
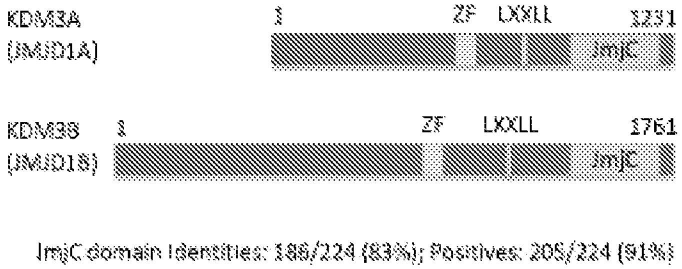
FIGS. 10A-B show images illustrating interaction of CBA-1 and KDM3B. (A) Domain identities of KDM3A and KDM3B. (B) Binding of CBA-1 to KDM3B.
Figure 10B:
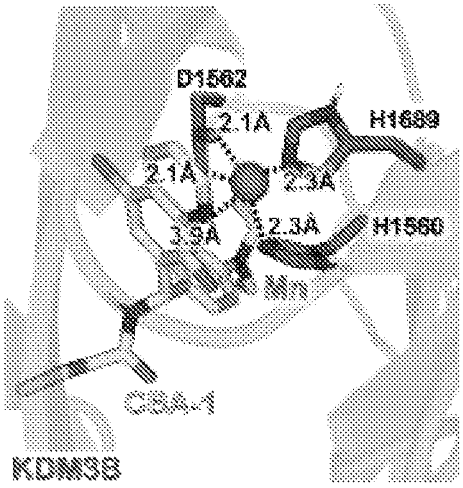

Other KDM3 members as CBA-1 targets. Inhibition of KDM3A by CBA-1 increased $H3K9Me^2$ and inhibited Wnt signaling; however, other KDM3 members may also regulate H3K9 methylation. For example, both KDM3B and KDM3C (JMJD1C) regulated Wnt signaling. Given the high similarity of their structures (FIG. 10A), particularly the JmjC domains, it is believed that CBA-1 would inhibit KDM3B and KDM3C as well. The present inventors recently found that CBA-1 weakly inhibits KDM3B at 10 μM. CBA-1 coordinated with $Mn^{2+}$ at a longer distance in KDM3B (3.9 Å) than the distance in KDM3A (2.8 Å) (FIGS. 8B and 10B). This could be one of the reasons that CBA-1 inhibited KDM3A better than KDM3B.

Since KDM3A is upregulated in CRC cells, it is expected that CRC cells or at least a subset of CRC cells will be more sensitive to CBA-1 than the normal colon cells. It is also expected that CBA-1 will increase repressive marker $H3K9Me^2$ and decrease active markers, H3K9Ac and $H3K4Me^3$, on the promoter of Wnt target genes in CRC cells. These markers will provide guidance for application of KDM3A inhibitors for CRC treatment.

Preclinical evaluation of KDM3A inhibitors using CRC organoids and PDX models. In preliminary studies, CBA-1 was established as a leading KDM3A inhibitor. From SAR and molecular docking studies, a CBA-1-like antibiotic, specifically, nitroxoline, was also identified as a point of comparison with our structurally related CBA analogs.

CBA-1 inhibited Wnt signaling in Zebrafish models. Zebrafish provide a well-established in vivo model to study Wnt signaling. Wnt signaling is active in the tail of the larvae during development (FIG. 4), and CBA-1 inhibited Wnt signaling in the tail. CBA-1 treatment also reduced Wnt-dependent tail regeneration. To rule out the possibility that CBA-1 inhibits the Wnt-mediated phenotype through nonspecific or even toxic effects, an eye-rescue experiment was performed. CBA-1 rescued Wnt-induced eye defects in a dose-responsive manner without obvious toxicity effects. These experiments suggest that CBA-1 inhibited Wnt signaling in vivo.

Figure 11A:
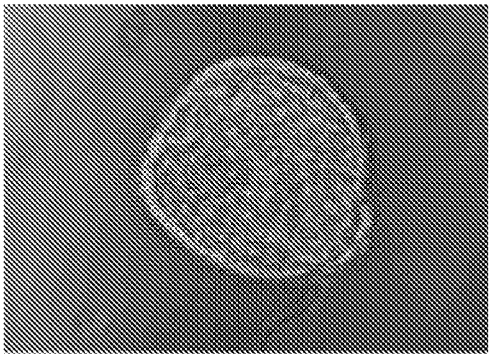
FIGS. 11A-B show an image and a graph illustrating mouse CRC organoids. (A) CRC organoids from $Apc^{fl/+}$/$Kras^{LsL-G12D}$/Villin-Cre mice. (B) CBA-1 (3 μM) inhibited CRC organoids (*p<0.01; n=3).
Figure 11B:
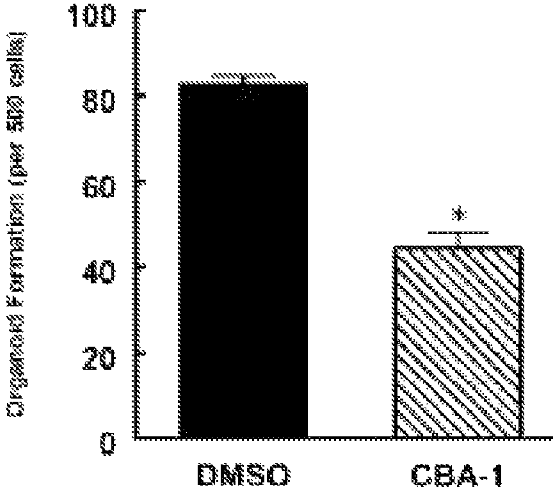

CRC organoids models. To analyze the effects of CBA-1 in CRC, a colon cancer organoid model was established from $Apc^{f/+}/Kras^{LSL-G12D}$/Villin-Cre mice (FIG. 11A). CBA-1 significantly inhibited mouse CRC organoids formation (FIG. 11B), suggesting that CBA-1 analogs and repurposed KDM3A inhibitors could inhibit CRC cells with APC and K-ras mutations.

Figure 12A:
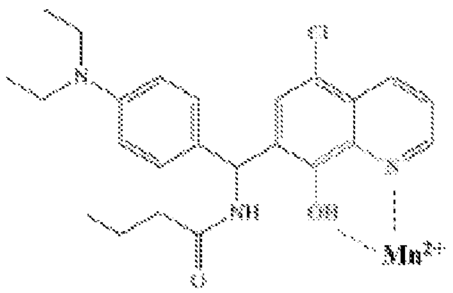
FIGS. 12A-E show images and graphs illustrating CBA-1 analogs from antibiotics. (A) Interaction of CBA-1 with $Mn^{2+}$. (B) Clioquinol (X=Cl; Y=I) and nitroxoline. (C-D) Inhibition of (C) KDM3A and (D) KDM3B enzymatic activities. (E) CBA-1 analogs (50 mg/kg, p.o.) inhibited LS174T CRC xenografts in SCID mice.
Figure 12B:
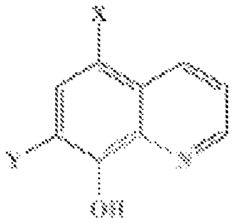
Figure 12C:
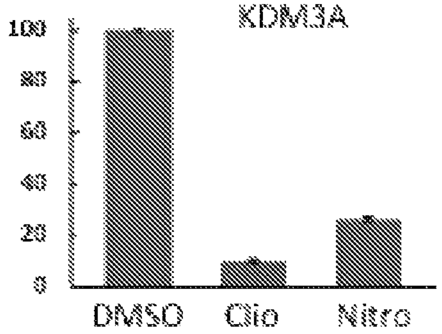
Figure 12D:
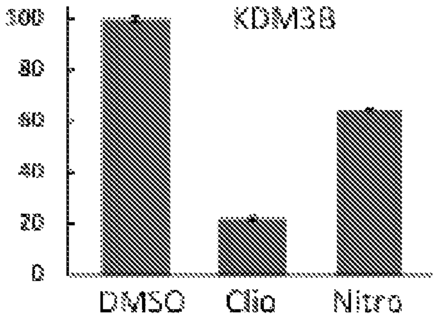
Figure 12E:
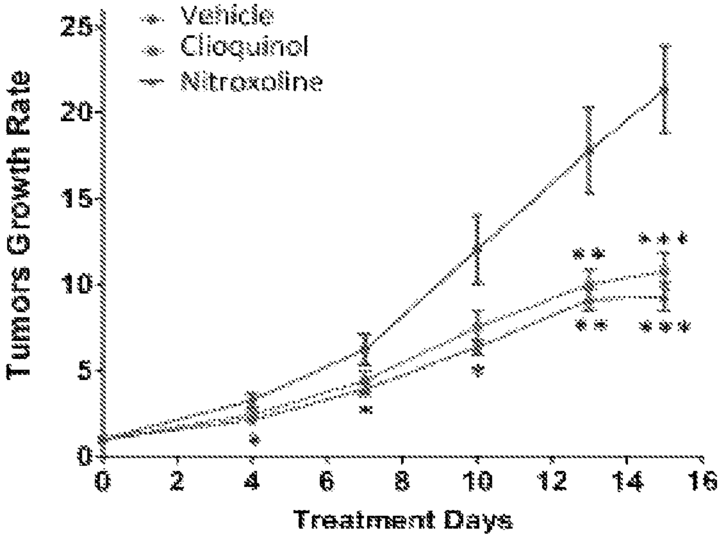

Repurposing drugs as CBA-1 analogs and KDM3 inhibitors. CBA-1 is a specific and potent KDM3A inhibitor. As backup candidates, two approved drugs were identified as CBA-1 analogs and KDM3A inhibitors. Based on the docking study (FIGS. 8A-B), the N and OH groups (red color in FIG. 12A) are critical in binding the $Mn^{2+}$ in KDM3A. In a SAR study, it was found that changes in the positions of these groups significantly reduced the KDM3A inhibition activity (data not shown). A virtual screening was performed and several antibiotics that have similar structures were identified. Two of these antibiotics, clioquinol and nitroxoline (FIG. 12B), indeed inhibited the enzymatic activities of KDM3 (FIGS. 12C and D). These two drugs were tested in LS174T tumor xenograft model in SCID mice. Both drugs inhibited tumor growth in LS174T tumor xenograft model in SCID mice (FIG. 12E). Nitroxoline has been used in Europe for over 50 years as an antibiotic. It has anticancer effects, but the mechanism remains unclear. Our findings suggest that CBA-1 analogs and repurposed KDM3 inhibitors can be used to treat KDM3 overexpressed cancers.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Liu, C.; Kato, Y.; Zhang, Z.; Do, V. M.; Yankner, B. A.; He, X., beta-Trcp couples beta-catenin phosphorylation-degradation and regulates Xenopus axis formation. *Proc Natl Acad Sc! USA* 1999, 96 (11), 6273-8.
2. Liu, C.; Li, Y.; Semenov, M.; Han, C.; Baeg, G. H.; Tan, Y.; Zhang, Z.; Lin, X.; He, X., Control of beta-catenin phosphorylation/degradation by a dual-kinase mechanism. *Cell* 2002, 108 (6), 837-47.

3. Shi, J.; Liu, Y.; Xu, X.; Zhang, W.; Yu, T.; Jia, J.; Liu, C., Deubiquitinase USP47/UBP64E Regulates beta-Catenin Ubiquitination and Degradation and Plays a Positive Role in Wnt Signaling. *Mol Cell B!ol* 2015, 35 (19), 3301-11.

4. Yang, J.; Zhang, W.; Evans, P. M.; Chen, X.; He, X.; Liu, C., Adenomatous polyposis coli (APC) differentially regulates beta-catenin phosphorylation and ubiquitination in colon cancer cells. *J B!ol Chem* 2006, 281 (26), 17751-7.

5. Zhang, W.; Sviripa, V. M.; Xie, Y.; Yu, T.; Haney, M. G.; Blackburn, J. S.; Adeniran, C. A.; Zhan, C. G.; Watt, D. S.; Liu, C., Epigenetic Regulation of Wnt Signaling by Carboxamide-Substituted Benzhydryl Amines that Function as Histone Demethylase Inhibitors. *!Sc!ence* 2020, 23 (12), 101795.

6. Zhang, W.; Sviripa, V.; Chen, X.; Shi, J.; Yu, T.; Hamza, A.; Ward, N. D.; Kril, L. M.; Vander Kooi, C. W.; Zhan, C. G.; Evers, B. M.; Watt, D. S.; Liu, C., Fluorinated N,N-dialkylaminostilbenes repress colon cancer by targeting methionine S-adenosyltransferase 2A. *ACS Chem B!ol* 2013, 8 (4), 796-803.

7. Giles, R. H.; van Es, J. H.; Clevers, H., Caught up in a Wnt storm: Wnt signaling in cancer. *B!och!m B!ophys Acta* 2003, 1653 (1), 1-24.

8. Kinzler, K. W.; Vogelstein, B., Lessons from hereditary colorectal cancer. *Cell* 1996, 87 (2), 159-70.

9. Polakis, P., Wnt signaling and cancer. *Genes Dev* 2000, 14 (15), 1837-51.

10. Anastas, J. N.; Moon, R. T., WNT signalling pathways as therapeutic targets in cancer. *Nat Rev Cancer* 2013, 13 (1), 11-26.

11. Nusse, R.; Clevers, H., Wnt/beta-Catenin Signaling, Disease, and Emerging Therapeutic Modalities. *Cell* 2017, 169 (6), 985-999.

12. Barker, N.; Clevers, H., Mining the Wnt pathway for cancer therapeutics. *Nat Rev Drug D!scov* 2006, 5 (12), 997-1014.

13. Garber, K., Drugging the Wnt pathway: problems and progress. *J Natl Cancer Inst* 2009, 101 (8), 548-50.

14. Zhong, Z.; Virshup, D. M., Wnt Signaling and Drug Resistance in Cancer. *Mol Pharmacol* 2020, 97 (2), 72-89.

15. Chen, B.; Dodge, M. E.; Tang, W.; Lu, J.; Ma, Z.; Fan, C. W.; Wei, S.; Hao, W.; Kilgore, J.; Williams, N. S.; Roth, M. G.; Amatruda, J. F.; Chen, C.; Lum, L., Small molecule-mediated disruption of Wnt-dependent signaling in tissue regeneration and cancer. *Nat Chem B!ol* 2009, 5 (2), 100-7.

16. Huang, S. M.; Mishina, Y. M.; Liu, S.; Cheung, A.; Stegmeier, F.; Michaud, G. A.; Charlat, O.; Wiellette, E.; Zhang, Y.; Wiessner, S.; Hild, M.; Shi, X.; Wilson, C. J.; Mickanin, C.; Myer, V.; Fazal, A.; Tomlinson, R.; Serluca, F.; Shao, W.; Cheng, H.; Shultz, M.; Rau, C.; Schirle, M.; Schlegl, J.; Ghidelli, S.; Fawell, S.; Lu, C.; Curtis, D.; Kirschner, M. W.; Lengauer, C.; Finan, P. M.; Tallarico, J. A.; Bouwmeester, T.; Porter, J. A.; Bauer, A.; Cong, F., Tankyrase inhibition stabilizes axin and antagonizes Wnt signalling. *Nature* 2009.

17. Liu, J.; Pan, S.; Hsieh, M. H.; Ng, N.; Sun, F.; Wang, T.; Kasibhatla, S.; Schuller, A. G.; Li, A. G.; Cheng, D.; Li, J.; Tompkins, C.; Pferdekamper, A.; Steffy, A.; Cheng, J.; Kowal, C.; Phung, V.; Guo, G.; Wang, Y.; Graham, M. P.; Flynn, S.; Brenner, J. C.; Li, C.; Villarroel, M. C.; Schultz, P. G.; Wu, X.; McNamara, P.; Sellers, W. R.; Petruzzelli, L.; Boral, A. L.; Seidel, H. M.; McLaughlin, M. E.; Che, J.; Carey, T. E.; Vanasse, G.; Harris, J. L., Targeting Wnt-driven cancer through the inhibition of Porcupine by LGK974. *Proc Natl Acad Sc! USA* 2013, 110 (50), 20224-9.

18. Lyou, Y.; Habowski, A. N.; Chen, G. T.; Waterman, M. L., Inhibition of nuclear Wnt signalling: challenges of an elusive target for cancer therapy. *Br J Pharmacol* 2017, 174 (24), 4589-4599.

19. Lee, E.; Madar, A.; David, G.; Garabedian, M. J.; Dasgupta, R.; Logan, S. K., Inhibition of androgen receptor and beta-catenin activity in prostate cancer. *Proc Natl Acad Sci USA* 2013, 110 (39), 15710-5.

20. Lepourcelet, M.; Chen, Y. N.; France, D. S.; Wang, H.; Crews, P.; Petersen, F.; Bruseo, C.; Wood, A. W.; Shivdasani, R. A., Small-molecule antagonists of the oncogenic Tcf/beta-catenin protein complex. *Cancer Cell* 2004, 5 (1), 91-102.

21. Schneider, J. A.; Craven, T. W.; Kasper, A. C.; Yun, C.; Haugbro, M.; Briggs, E. M.; Svetlov, V.; Nudler, E.; Knaut, H.; Bonneau, R.; Garabedian, M. J.; Kirshenbaum, K.; Logan, S. K., Design of Peptoid-peptide Macrocycles to Inhibit the beta-catenin TCF Interaction in Prostate Cancer. *Nat Commun* 2018, 9 (1), 4396.

22. Feng, M.; Jin, J. Q.; Xia, L.; Xiao, T.; Mei, S.; Wang, X.; Huang, X.; Chen, J.; Liu, M.; Chen, C.; Rafi, S.; Zhu, A. X.; Feng, Y. X.; Zhu, D., Pharmacological inhibition of beta-catenin/BCL9 interaction overcomes resistance to immune checkpoint blockades by modulating Treg cells. *Sci Adv* 2019, 5 (5), eaau5240.

23. Wisniewski, J. A.; Yin, J.; Teuscher, K. B.; Zhang, M.; Ji, H., Structure-Based Design of 1,4-Dibenzoylpiperazines as beta-Catenin/B-Cell Lymphoma 9 Protein-Protein Interaction Inhibitors. *ACS Med Chem Lett* 2016, 7 (5), 508-13.

24. Emami, K. H.; Nguyen, C.; Ma, H.; Kim, D. H.; Jeong, K. W.; Eguchi, M.; Moon, R. T.; Teo, J. L.; Kim, H. Y.; Moon, S. H.; Ha, J. R.; Kahn, M., A small molecule inhibitor of beta-catenin/CREB-binding protein transcription [corrected]. *Proc Natl Acad Sci USA* 2004, 101 (34), 12682-7.

25. Lenz, H. J.; Kahn, M., Safely targeting cancer stem cells via selective catenin coactivator antagonism. *Cancer Sci* 2014, 105 (9), 1087-92.

26. Zhang, W.; Sviripa, V. M.; Kril, L. M.; Yu, T.; Xie, Y.; Hubbard, W. B.; Sullivan, P. G.; Chen, X.; Zhan, C. G.; Yang-Hartwich, Y.; Evers, B. M.; Spear, B. T.; Gedaly, R.; Watt, D. S.; Liu, C., An Underlying Mechanism of Dual Wnt Inhibition and AMPK Activation: Mitochondrial Uncouplers Masquerading as Wnt Inhibitors. *J Med Chem* 2019, 62 (24), 11348-11358.

27. Sierra, J.; Yoshida, T.; Joazeiro, C. A.; Jones, K. A., The APC tumor suppressor counteracts beta-catenin activation and H3K4 methylation at Wnt target genes. *Genes & development* 2006, 20 (5), 586-600.

28. Cloos, P. A.; Christensen, J.; Agger, K.; Helin, K., Erasing the methyl mark: histone demethylases at the center of cellular differentiation and disease. *Genes & development* 2008, 22 (9), 1115-40.

29. Jambhekar, A.; Anastas, J. N.; Shi, Y., Histone Lysine Demethylase Inhibitors. *Cold Spring Harb Perspect Med* 2017, 7 (1).

30. Klose, R. J.; Kallin, E. M.; Zhang, Y., JmjC-domain-containing proteins and histone demethylation. *Nat Rev Genet* 2006, 7 (9), 715-27.

31. Shi, Y.; Lan, F.; Matson, C.; Mulligan, P.; Whetstine, J. R.; Cole, P. A.; Casero, R. A.; Shi, Y., Histone demethylation mediated by the nuclear amine oxidase homolog LSD1. *Cell* 2004, 119 (7), 941-53.

32. Kooistra, S. M.; Helin, K., Molecular mechanisms and potential functions of histone demethylases. *Nat Rev Mol Cell Biol* 2012, 13 (5), 297-311.

33. Sviripa, V. M.; Zhang, W.; Balia, A. G.; Tsodikov, O. V.; Nickell, J. R.; Gizard, F.; Yu, T.; Lee, E. Y.; Dwoskin, L. P.; Liu, C.; Watt, D. S., 2',6'-Dihalostyrylanilines, pyridines, and pyrimidines for the inhibition of the catalytic subunit of methionine S-adenosyltransferase-2. *J Med Chem* 2014, 57 (14), 6083-91.

34. MacDonald, B. T.; Tamai, K.; He, X., Wnt/beta-Catenin Signaling: Components, Mechanisms, and Diseases. *Developmental Cell* 2009, 17 (1), 9-26.

35. Comprehensive molecular characterization of human colon and rectal cancer. *Nature* 2012, 487 (7407), 330-7.

36. Schatoff, E. M.; Leach, B. I.; Dow, L. E., Wnt Signaling and Colorectal Cancer. *Current colorectal cancer reports* 2017, 13 (2), 101-110.

37. Patnaik, S.; Anupriya, Drugs Targeting Epigenetic Modifications and Plausible Therapeutic Strategies Against Colorectal Cancer. *Front Pharmacol* 2019, 10, 588.

38. Polakis, P., Wnt signaling in cancer. *Cold Spring Harb Perspect Biol* 2012, 4 (5).

39. Strekalova, E.; Malin, D.; Weisenhorn, E. M. M.; Russell, J. D.; Hoelper, D.; Jain, A.; Coon, J. J.; Lewis, P. W.; Cryns, V. L., S-adenosylmethionine biosynthesis is a targetable metabolic vulnerability of cancer stem cells. *Breast Cancer Res Treat* 2019, 175 (1), 39-50.

40. Zhang, W.; Sviripa, V.; Kril, L. M.; Chen, X.; Yu, T.; Shi, J.; Rychahou, P.; Evers, B. M.; Watt, D. S.; Liu, C., Fluorinated N,N-dialkylaminostilbenes for Wnt pathway inhibition and colon cancer repression. *J Med Chem* 2011, 54 (5), 1288-97.

41. Zaytseva, Y. Y.; Rychahou, P. G.; Le, A. T.; Scott, T. L.; Flight, R. M.; Kim, J. T.; Harris, J.; Liu, J.; Wang, C.; Morris, A. J.; Sivakumaran, T. A.; Fan, T.; Moseley, H.; Gao, T.; Lee, E. Y.; Weiss, H. L.; Heuer, T. S.; Kemble, G.; Evers, M., Preclinical evaluation of novel fatty acid synthase inhibitors in primary colorectal cancer cells and a patient-derived xenograft model of colorectal cancer. *Oncotarget* 2018, 9 (37), 24787-24800.

42. Hedgepeth, C. M.; Conrad, L. J.; Zhang, J.; Huang, H. C.; Lee, V. M.; Klein, P. S., Activation of the Wnt signaling pathway: a molecular mechanism for lithium action. *Dev Biol* 1997, 185 (1), 82-91.

43. Peng, K.; Su, G.; Ji, J.; Yang, X.; Miao, M.; Mo, P.; Li, M.; Xu, J.; Li, W.; Yu, C., Histone demethylase JMJD1A promotes colorectal cancer growth and metastasis by enhancing Wnt/beta-catenin signaling. *J Biol Chem* 2018, 293 (27), 10606-10619.

44. Liu, J.; Liang, T.; Zhangsun, W., KDM3A is associated with tumor metastasis and modulates colorectal cancer cell migration and invasion. *Int J Biol Macromol* 2019, 126, 318-325.

45. Li, J.; Yu, B.; Deng, P.; Cheng, Y.; Yu, Y.; Kevork, K.; Ramadoss, S.; Ding, X.; Li, X.; Wang, C. Y., KDM3 epigenetically controls tumorigenic potentials of human colorectal cancer stem cells through Wnt/beta-catenin signalling. *Nat Commun* 2017, 8, 15146.

46. Wang, H. Y.; Long, Q. Y.; Tang, S. B.; Xiao, Q.; Gao, C.; Zhao, Q. Y.; Li, Q. L.; Ye, M.; Zhang, L.; Li, L. Y.; Wu, M., Histone demethylase KDM3A is required for enhancer activation of hippo target genes in colorectal cancer. *Nucleic Acids Res* 2019, 47 (5), 2349-2364.

47. Evans, P. M.; Chen, X.; Zhang, W.; Liu, C., KLF4 interacts with beta-catenin/TCF4 and blocks p300/CBP recruitment by beta-catenin. *Mol Cell Biol* 2010, 30 (2), 372-81.

48. Evans, P. M.; Zhang, W.; Chen, X.; Yang, J.; Bhakat, K. K.; Liu, C., Kruppel-like factor 4 is acetylated by p300 and regulates gene transcription via modulation of histone acetylation. *J Biol Chem* 2007, 282 (47), 33994-4002.

49. Yu, T.; Chen, X.; Zhang, W.; Colon, D.; Shi, J.; Napier, D.; Rychahou, P.; Lu, W.; Lee, E. Y.; Weiss, H. L.; Evers, B. M.; Liu, C., Regulation of the potential marker for intestinal cells, Bmil, by beta-catenin and the zinc finger protein KLF4: implications for colon cancer. *J Biol Chem* 2012, 287 (6), 3760-8.

50. Burikhanov, R.; Sviripa, V. M.; Hebbar, N.; Zhang, W.; Layton, W. J.; Hamza, A.; Zhan, C. G.; Watt, D. S.; Liu, C.; Rangnekar, V. M., Arylquins target vimentin to trigger Par-4 secretion for tumor cell apoptosis. *Nat Chem Biol* 2014, 10 (11), 924-926.

51. Frasinyuk, M. S.; Zhang, W.; Wyrebek, P.; Yu, T.; Xu, X.; Sviripa, V. M.; Bondarenko, S. P.; Xie, Y.; Ngo, H. X.; Morris, A. J.; Mohler, J. L.; Fiandalo, M. V.; Watt, D. S.; Liu, C., Developing antineoplastic agents that target peroxisomal enzymes: cytisine-linked isoflavonoids as inhibitors of hydroxysteroid 17-beta-dehydrogenase-4 (HSD17B4). *Org Biomol Chem* 2017, 15 (36), 7623-7629.

52. Berg, K. C. G.; Eide, P. W.; Eilertsen, I. A.; Johannessen, B.; Bruun, J.; Danielsen, S. A.; Bjornslett, M.; Meza-Zepeda, L. A.; Eknaes, M.; Lind, G. E.; Myklebost, O.; Skotheim, R. I.; Sveen, A.; Lothe, R. A., Multi-omics of 34 colorectal cancer cell lines—a resource for biomedical studies. *Mol Cancer* 2017, 16 (1), 116.

53. Barretina, J.; Caponigro, G.; Stransky, N.; Venkatesan, K.; Margolin, A. A.; Kim, S.; Wilson, C. J.; Lehar, J.; Kryukov, G. V.; Sonkin, D.; Reddy, A.; Liu, M.; Murray, L.; Berger, M. F.; Monahan, J. E.; Morais, P.; Meltzer, J.; Korejwa, A.; Jane-Valbuena, J.; Mapa, F. A.; Thibault, J.; Bric-Furlong, E.; Raman, P.; Shipway, A.; Engels, I. H.; Cheng, J.; Yu, G. K.; Yu, J.; Aspesi, P., Jr.; de Silva, M.; Jagtap, K.; Jones, M. D.; Wang, L.; Hatton, C.; Palescandolo, E.; Gupta, S.; Mahan, S.; Sougnez, C.; Onofrio, R. C.; Liefeld, T.; MacConaill, L.; Winckler, W.; Reich, M.; Li, N.; Mesirov, J. P.; Gabriel, S. B.; Getz, G.; Ardlie, K.; Chan, V.; Myer, V. E.; Weber, B. L.; Porter, J.; Warmuth, M.; Finan, P.; Harris, J. L.; Meyerson, M.; Golub, T. R.; Morrissey, M. P.; Sellers, W. R.; Schlegel, R.; Garraway, L. A., The Cancer Cell Line Encyclopedia enables predictive modelling of anticancer drug sensitivity. *Nature* 2012, 483 (7391), 603-7.

54. Wen, Y. A.; Xing, X.; Harris, J. W.; Zaytseva, Y. Y.; Mitov, M. I.; Napier, D. L.; Weiss, H. L.; Mark Evers, B.; Gao, T., Adipocytes activate mitochondrial fatty acid oxidation and autophagy to promote tumor growth in colon cancer. *Cell Death Dis* 2017, 8 (2), e2593.
55. Veschi, S.; De Lellis, L.; Florio, R.; Lanuti, P.; Massucci, A.; Tinari, N.; De Tursi, M.; di Sebastiano, P.; Marchisio, M.; Natoli, C.; Cama, A., Effects of repurposed drug candidates nitroxoline and nelfinavir as single agents or in combination with erlotinib in pancreatic cancer cells. *J Exp Clin Cancer Res* 2018, 37 (1), 236.
56. Xie, Y.; Kril, L. M.; Yu, T.; Zhang, W.; Frasinyuk, M. S.; Bondarenko, S. P.; Kondratyuk, K. M.; Hausman, E.; Martin, Z. M.; Wyrebek, P. P.; Liu, X.; Deaciuc, A.; Dwoskin, L. P.; Chen, J.; Zhu, H.; Zhan, C. G.; Sviripa, V. M.; Blackburn, J.; Watt, D. S.; Liu, C., Semisynthetic aurones inhibit tubulin polymerization at the colchicine-binding site and repress PC-3 tumor xenografts in nude mice and myc-induced T-ALL in zebrafish. *Sci Rep* 2019, 9 (1), 6439.
57. Wen, Y. A.; Xiong, X.; Zaytseva, Y. Y.; Napier, D. L.; Vallee, E.; Li, A. T.; Wang, C.; Weiss, H. L.; Evers, B. M.; Gao, T., Downregulation of SREBP inhibits tumor growth and initiation by altering cellular metabolism in colon cancer. *Cell death & disease* 2018, 9 (3), 265.
58. Kondo, J.; Endo, H.; Okuyama, H.; Ishikawa, O.; Iishi, H.; Tsujii, M.; Ohue, M.; Inoue, M., Retaining cell-cell contact enables preparation and culture of spheroids composed of pure primary cancer cells from colorectal cancer. *Proc Natl Acad Sci USA* 2011, 108 (15), 6235-40.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A compound for inhibiting Wnt signaling, the compound comprising a structure according to Formula II:

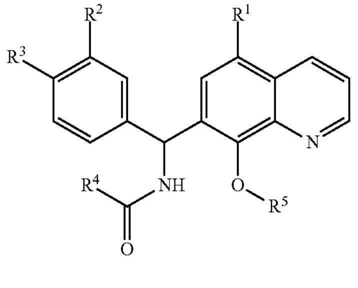

II wherein $R^1$ is selected from the group consisting of H, Cl, and nitrite;

wherein $R^2$ is selected from the group consisting of H and alkoxy;

wherein $R^3$ is a heterocycle, the heterocycle selected from the group consisting of pyrrolidinyl, piperidinyl, and morpholino;

wherein $R^4$ is selected from the group consisting of substituted or unsubstituted, branched or unbranched alkyl; and wherein $R^5$ is selected from the group consisting of H and methyl carbonyl.

2. The compound of claim 1, wherein $R^1$ is Cl.

3. The compound of claim 2, wherein $R^5$ is H.

4. The compound of claim 3, wherein $R^2$ is H.

5. The compound of claim 4, wherein $R^4$ is an unbranched alkyl.

6. The compound of claim 4, wherein $R^4$ is a branched alkyl.

7. A compound for inhibiting Wnt signaling, the compound is-selected from the group consisting of:

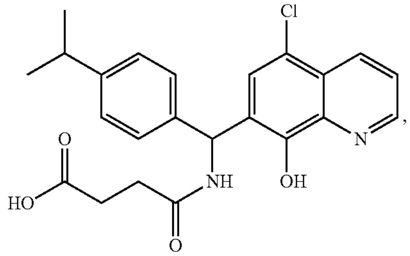,

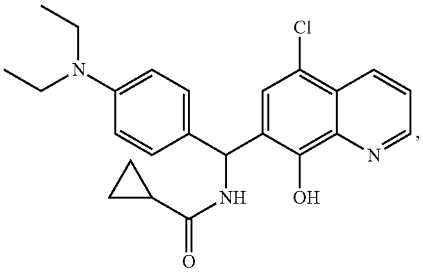,

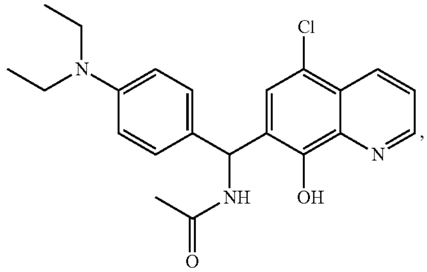,

-continued
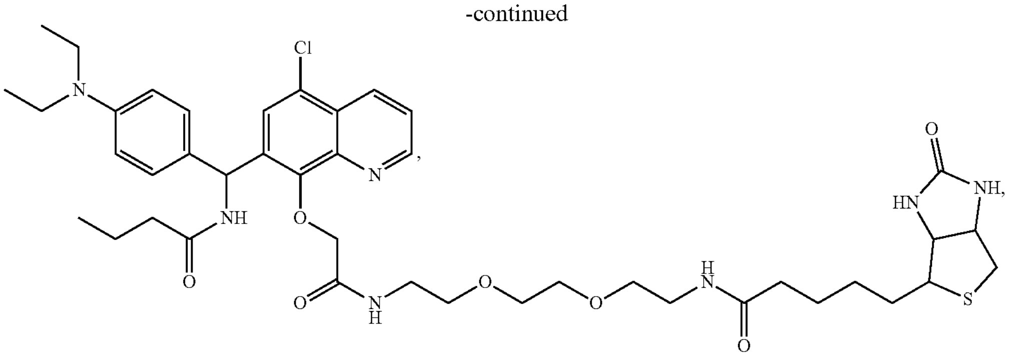,
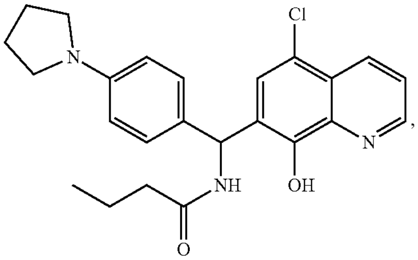, 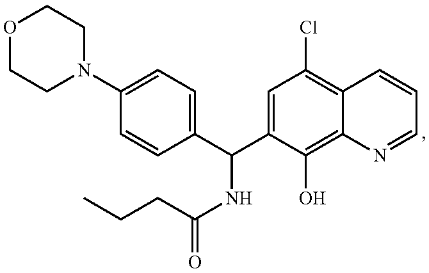,
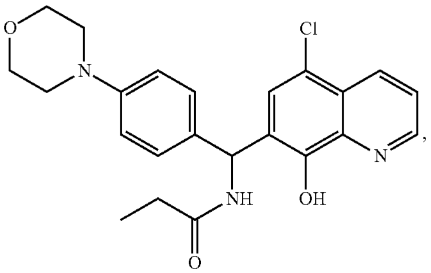, and 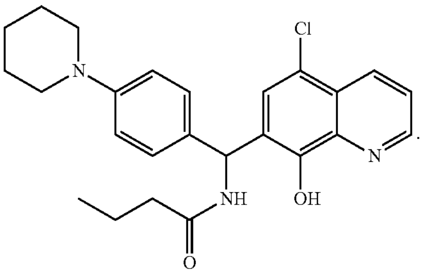.
8. A method of treating cancer, the method comprising administering, to a subject in need thereof, a compound selected from the group consisting of:
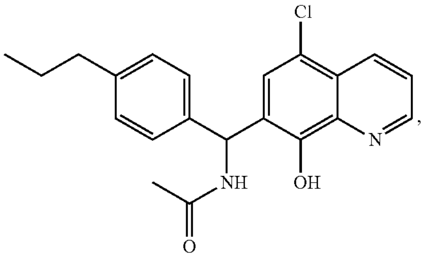, 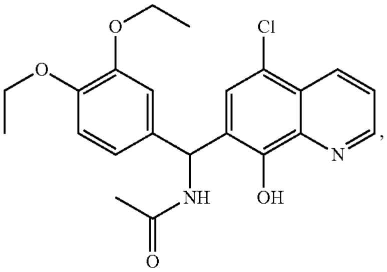,
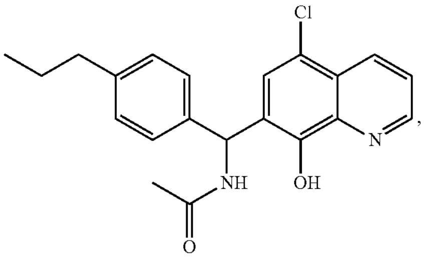, 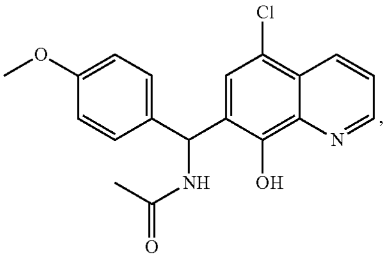, -continued
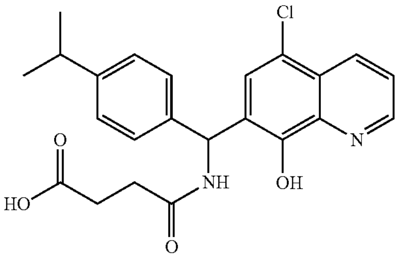,
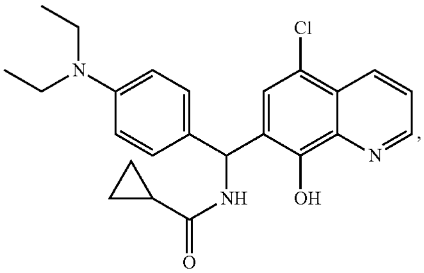,
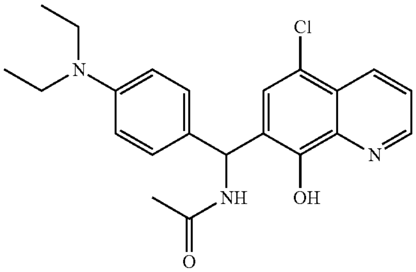,
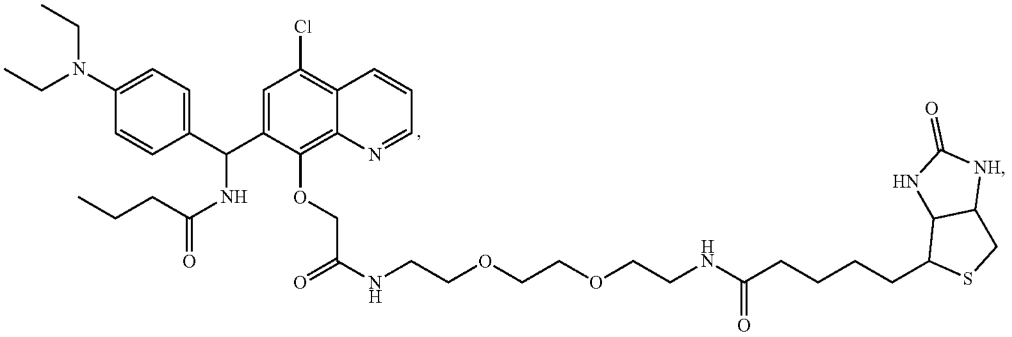
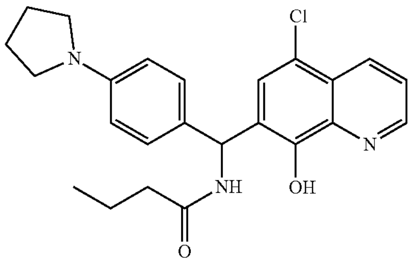,
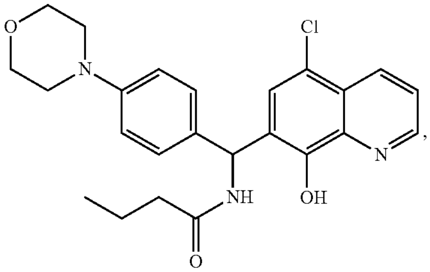,
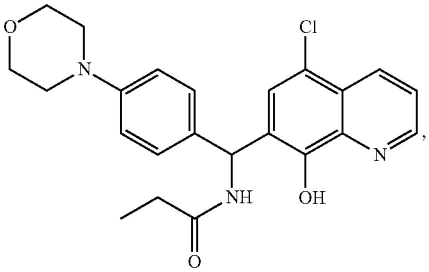, and
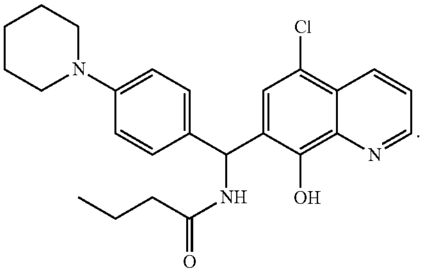.

9. The method of claim 8, further comprising administering to the subject another compound selected from the group consisting of:
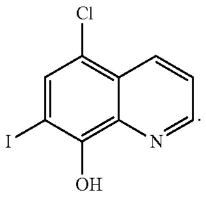
and
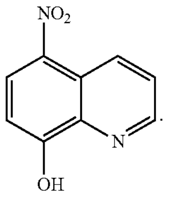
10. The method of claim 8, wherein the subject has cancer.
* * * * *